US008008341B2

(12) United States Patent
Halazy et al.

(10) Patent No.: US 8,008,341 B2
(45) Date of Patent: Aug. 30, 2011

(54) PHARMACEUTICALLY ACTIVE BENZSULFONAMIDE DERIVATIVES AS INHIBITORS OF PROTEIN JUNKINASES

(75) Inventors: Serge Halazy, Vetraz-Monthoux (FR); Dennis Church, Commugny (CH); Stephen J. Arkinstall, Belmont, MA (US); Marco Biamonte, San Diego, CA (US); Montserrat Camps, Versoix (CH); Jean-Pierre Gotteland, Beaumont (FR); Thomas Rueckle, Plan-les-Ouates (CH)

(73) Assignee: Merck Serono SA, Vaud (CH)

( * ) Notice: Subject to any disclaimer, the term of this patent is extended or adjusted under 35 U.S.C. 154(b) by 143 days.

(21) Appl. No.: 12/142,296

(22) Filed: Jun. 19, 2008

(65) Prior Publication Data

US 2008/0255222 A1  Oct. 16, 2008

Related U.S. Application Data

(62) Division of application No. 10/381,197, filed as application No. PCT/IB01/01773 on Sep. 27, 2001, now Pat. No. 7,417,058.

(30) Foreign Application Priority Data

Sep. 27, 2000 (EP) .................................... 00810888

(51) Int. Cl.
  *A61P 25/00* (2006.01)
  *A61P 37/00* (2006.01)
  *A61K 31/4468* (2006.01)
  *C07D 211/96* (2006.01)
(52) U.S. Cl. .................. 514/424; 514/425; 548/542
(58) Field of Classification Search .................. 514/424, 514/425; 548/542
See application file for complete search history.

(56) References Cited

U.S. PATENT DOCUMENTS

| 3,812,144 A | 5/1974 | Dietrich et al. |
| 5,744,320 A | 4/1998 | Sherf et al. |
| 2004/0077632 A1 | 4/2004 | Halazy et al. |
| 2004/0077854 A1 | 4/2004 | Halazy et al. |

OTHER PUBLICATIONS

Debnath et al., 4-(4'-Substituted benzoyl)aminobenzenesulphonyl-L(+)-glutamic acids and 5-N-substituted-2-[4'-(4"-substituted benzoyl)aminobenzenesulphonyl]-L-glutamines as potential antineoplastic agents, Indian Journal of Chemistry, vol. 28B, No. 10, pp. 843-847, 1989.*
U.S. Appl. No. 10/070,954, filed Sep. 28, 2000, Halazy, et al.
U.S. Appl. No. 10/088,074, filed Oct. 13, 2004, Arkinstall, et al.
U.S. Appl. No. 12/172,485, Jul. 14, 2008, Arkinstall, et al.
U.S. Appl. No. 10/088,090, Jun. 21, 2002, Arkinstall, et al.
U.S. Appl. No. 12/565,988, filed Sep. 24, 2009, Rueckle, et al.

Database HCA 'Online! Chemical Abstracts Service, Columbus, OH, US; abstract No. 125:2165, XP002162517, 1996.
Roger J. Davis: "Signal transduction by the JNK Group of MAP kinases" Cell, vol. 103, pp. 239-252, 2000.
Yi-Rong Chen, et al: "The c-Jun N-terminal kinase pathway and apoptotic signaling" International Journal of Oncology, vol. 16, pp. 651-662, 2000.
YT IP et al: "Signal transduction by the c-Jun N-terminal kinase (JNK) from c-Jun N-terminal kinase (JNK) from inflammation to development" Curr Opin Cell Biol, vol. 10, pp. 205-219, 1998.
S. Leppa et al.: "Diverse functions of JNK signaling and c-Jun in stress response and apoptosis" Oncogene, vol. 18, No. 45, pp. 6158-6162, 1999.
A. Minden et al: "Regulation and function if the JNK subgroup of MAP kinases" Biochim Biophys Acta, vol. 1333, pp. F85-F104, 1997.
A.J. Whitmarsh et al.: "Transcription factor AP-1: regulation by mitogen activated protein kinases signal transduction pathways" J. Mol. Med., vol. 77, pp. 589-607, 1996.
S. Gupta et al.: Selective interation of JNK protein kinase isoforms with trascription factors, The EMBO Journal, vol. 158, No. 11, pp. 2760-2770, 1996.
D. Derek, et al.: "Absence of excitotoxicity-induced apoptosis in the hippocampus of mice lacking the Jnk3 gene" Nature, vol. 389, pp. 865-876, 1997.
Loel H. Martin et al.: "Development expression in the mouse nervous system of the p493F12 SAP kinase" Molecular Brain Research, vol. 35, pp. 47-57, 1996.
Y. Kumagae et al.: "Human c-Jun N-terminal kinase expression and activation in the nervous system" Molecular Brain Research, vol. 67, pp. 10-17, 1999.
Calin D. Dumitru et al.: "TNF-alpha induction by LPS is regulated posttranscriptionally via a Tpl2/ERK-dependent pathway" Cell, vol. 103, pp. 1071-1083, 2000.
Z. Han et al.: "C-Jun N-terminal kinase is required for metalloproteinase expression and joint destruction in inflammatory arthritis" The Journal of Clinical Investigation, vol. 108, No. 1, pp. 73-81, 2001.

(Continued)

Primary Examiner — Brenda Coleman
(74) Attorney, Agent, or Firm — Oblon, Spivak, McClelland, Maier & Neustadt, L.L.P.

(57) ABSTRACT

The present invention relates to benzsulfonamide derivatives of formula I and methods of use thereof. The benzsulfonamide derivatives of the present invention are efficient modulators of the JNK pathway. In particular the benzsulfonamide derivatives of the present invention are selective inhibitors of JNK 2 and 3.

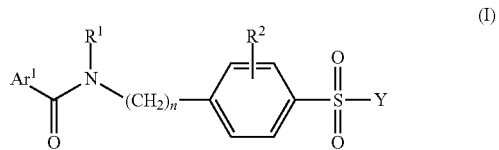

(I)

10 Claims, No Drawings

OTHER PUBLICATIONS

H. Nishina et al.: "Impaired CD28-mediated interleukin 2 production and proliferation in stress kinase SAPK/ERK1 kinase (SEK1)/mitogen-activated protein kinase kinase 4 (MKK4)-dificent T lymphocytes" Journal of Experimental Medicine, vol. 186, No. 6, pp. 941-953, 1997.

Stephan J. Kempiak et al.: "The Jun kinase cascade is responsible for activating the CD28 response element of the IL-2 promoter: proof of cross-talk with the IB kinase cascade" The Journal of Immunology, vol. 162, pp. 3176-3187, 1999.

S.M. De La Monte et al.: "Oxygen free radical injury is sufficient to cause some Alzheimer-type molecular abnormalities in human CNS neuronal cells" J. Alzheimer's Dis., vol. 2, No. 3-4, pp. 261-281, 2000.

X. Zhu: "Activation and redistribution of c-Jun N-terminal kinase/stress activated protein kinase in degenerating neurons in Alzheimer's disease" Journal of Neurochemistry, vol. 76, pp. 435-441, 2001.

T. Force et al.: "Stress-activated protein kinases in cardiovascular disease" Circulation Research, vol. 78, pp. 947-953, 1996.

S. Kim et al.: "Angiotensin blockade inhibits activation of mitogen-activated protein kinases in rat balloon-injured artery" Circulation, vol. 97, pp. 1731-1737, 1998.

Q. Xu et al.: "Acute hypertension activates mitogen-activated protein kinases in arterial wall" The Journal of Clinical Investigation, vol. 97, No. 2, pp. 508-514, 1996.

M. A. Bogoyevitch, et al.: "Stimulation of the stress-activated mitogen-activated protein kinase subfamilies in perfused heart" Circulation Research, vol. 79, pp. 163-173, 1996.

CM Pombo et al.: "The stress-activated protein kinases are major c-Jun amino-terminal kinases activated by ischemia and reperfusion" J. Biol. Chem., vol. 42, pp. 26546-26551, 1994.

I. Onishi et al.: "Activation of c-Jun N-terminal kinase during ischemia and reperfusion in mouse liver" FEBS Letters, vol. 420, pp. 201-204, 1997.

R. Safirstein: "Renal stress response and acute renal failure" Adv. Ren. Replace Ther., vol. 4, No. 2 Suppl 1, pp. 38-42, 1997.

L. Butterfield, et al.: "C-Jun NH2-terminal kinase regulation of the apoptotic response of small cell lung cancer cells to ultraviolet radiation" The Journal of Biological Chemistry, vol. 272, No. 15, pp. 10110-10116, 1997.

M. Hu et al.: JNK2 and JNK3 are p53 N-terminal serine 34 kinases Oncogene, vol. 15, pp. 2277-2287, 1997.

X. Xu et al.: Constitutively activated JNK is associated with HTLV-1 mediated tumorgenesis, Oncogene, vol. 13, pp. 135-142, 1996.

YR Chen et al.: The c-Jun N-terminal kinase pathway and apoptotic signaling Int. J. Oncol., vol. 16, No. 4, pp. 651-662, 2000.

T.C. Harding et al.: "Inhibition of JNK by overexpression of the JNK binding domain of JIP-1 prevents apoptosis in sympathetic neurons" The Journal of Biological Chemistry, vol. 276, No. 7, pp. 4531-4534, 2001.

AF Abdel-Magid et al.: "Reductive amination of aldehves and ketones with sodium triacetoxyborohydride. Studies on direct and indirect reductive amination procedures" Journal of Organic Chemistry, vol. 61, pp. 3849-3862, 1996.

L. Xu et al.: "Assess the in-vivo activation of signal transduction pathways with Pathdetect® reporting systems" Strategies, vol. 14, No. 1, pp. 1-3, 2001.

A.M. Manning, et al., "Targeting JNK for Therapeutic Benefit: From Junk to Gold?," Nature, vol. 2, Jul. 2003, pp. 554-565.

P.A. Scherle, et al., "Kinase Targets in Inflammation," Emerging Therapeutic Targets, vol. 3, No. 1, 1999, pp. 1-25.

* cited by examiner

PHARMACEUTICALLY ACTIVE BENZSULFONAMIDE DERIVATIVES AS INHIBITORS OF PROTEIN JUNKINASES

CROSS-REFERENCE TO RELATED APPLICATIONS

The present application is divisional of U.S. 10/381,197, filed on Sep. 8, 2003, which is a National Stage (371) of PCT/IB01/01773, filed on Sep. 27, 2001, and claims priority to EP 00810888.8, filed on Sep. 27, 2000.

FIELD OF THE INVENTION

The present invention is related to benzsulfonamides. Said sulfonamide derivatives are notably for use as pharmaceutically active compounds. Also, the present invention is related to pharmaceutical formulations containing such sulfonamide derivatives. In particular, the present invention is related to sulfonamide derivatives that are useful in the treatment and/or prevention of disorders of the immune and the neuronal system. Specifically, the sulfonamide derivatives of the present invention display a substantial modulatory, notably an inhibitory activity of the JNK (Jun-Kinase) function or pathways respectively.

BACKGROUND OF THE INVENTION

Apoptosis denotes the complex contortions of the membrane and organelles of a cell as it undergoes the process of programmed cell death. During said process, the cell activates an intrinsic suicide program and systematically destroys itself. The following series of events can be observed:

The cell surface begins to bleb and expresses pro-phagocytic signals. The whole apoptotic cell then fragments into membrane-bound vesicles that are rapidly and neatly disposed of by phagocytosis, so that there is minimal damage to the surrounding tissue.

The cell then separates from its neighbors.

The nucleus also goes through a characteristic pattern of morphological changes as it commits genetic suicide, the chromatin condenses and is specifically cleaved to fragments of DNA.

Neuronal cell death plays an important role in ensuring that the nervous system develops normally. It appears that the death of developing neurons depends on the size of the target that they innervate: cells with fewer synaptic partners are more likely to die than those that have formed multiple synapses. This may reflect a process, which balances the relative number of pre- to postsynaptic neurons in the developing nervous system. Although neuronal cell death was assumed to be apoptotic, it was only recently that neurons in developing rodent brain were conclusively shown to undergo apoptosis as classified by morphology and DNA fragmentation. As cell death during development is clearly not a pathological process, it makes sense that cells actually cease to exist.

Neuronal death occurs via either apoptotic or necrotic processes following traumatic nerve injury or during neurodegenerative diseases. Multiple components are emerging as key players having a role in driving neuronal programmed cell death. Amongst the components leading to neuronal apoptosis are members of the SAPK/JNK being a sub-family of MAP Kinases (MAPKs).

Mammalian cells respond to some extracellular stimuli by activating signaling cascades which are mediated by various mitogen-activated protein kinases (MAPKs). Despite the differences in their response to upstream stimuli, the MAP kinase cascades are organized in a similar fashion, consisting of MAP kinase kinase kinases (MAPKKK or MEKK), MAP kinase kinases (MAPKK or MKK) and MAP kinases (MAPK). MAP kinases are a broad family of kinases which includes c-Jun N-Terminal kinases (JNKs), also known as "stress-activated protein kinases" (SAPKs), as well as extra-cellular signal regulated kinases (ERKs) and p38 MAP kinases. Each of these three MAP kinases sub-families is involved in at least three different but parallel pathways conveying the information triggered by external stimuli. The JNK signaling pathway is activated by exposure of cells to environmental stress—such as chemical toxins, radiation, hypoxia and osmotic shock—as well as by treatment of cells with growth factors or pro-inflammatory cytokines—such as tumour necrosis factor alpha (TNF-α) or interleukin-1 beta (IL-1β).

Two MAP kinase kinases (known as MKKs or MAPKKs), i.e. MKK4 (known also as JNKK1) and MKK7 (known also as JNKK2), activate JNK by a dual phosphorylation of specific threonine and tyrosine residues located within a Thr-Pro-Tyr motif on the activation loop on the enzyme, in response to cytokines and stress signals. Even further upstream in the signaling cascade, MKK4 is known to be activated itself also by a MAP kinase kinase kinase, MEKK1 through phosphorylation at serine and threonine residues.

Once activated, JNK binds to the N-terminal region of transcription factor targets and phosphorylates the transcriptional activation domains resulting in the up-regulation of expression of various gene products, which can lead to apoptosis, inflammatory responses or oncogenic processes (1-5).

MAPKs (mitogen-activated protein kinases) are serine/threonine kinases that are activated by dual phosphorylation on threonine and tyrosine residues. In mammalian cells, there are at least three separate but parallel pathways that convey information generated by extra-cellular stimuli to the MAPKs. Said pathways consist of kinase cascades leading to activation of the ERKs (extracellular regulated kinases), the JNKs (c-Jun N-terminal kinases), and the p38/CSBP kinases. While both the JNK and p38 pathways are involved in relaying stress-type extramolecular signals, the ERK pathway is primarily responsible for transducing mitogenic/differentiation signals to the cell nucleus.

SAPK cascades represent a sub-family of the mitogen-activating protein kinase family, that are activated by different external stimuli including DNA damage following UV irradiation, TNF-α, IL-1β, ceramide, cellular stress, and reactive oxygen species and have distinct substrate specificities. Signal transduction via MKK4/JNK of MKK3/p38 results in the phosphorylation of inducible transcription factors, c-Jun and ATF2, which then act as either homodimers or heterodimers to initiate transcription of down-stream effectors.

c-Jun is a protein that is forming homodimers and heterodimers (with e.g. c-Fos) to produce the transactivating complex AP—which is required for the activation of many genes (e.g. matrix metalloproteinases) involved in the inflammatory response. The JNKs were discovered when it was found that several different stimuli such as UV light and TNF-α stimulated phosphorylation of c-Jun on specific serine residues in the N-terminus of the protein.

Three distinct JNK enzymes have been identified as products of the genes JNK1, JNK2 and JNK3 and ten different isoforms of JNK have been identified (3, 6, 7). JNK1 and -2 are ubiquitously expressed in human tissues, whereas JNK3 is selectively expressed in the brain, heart and testes (7, 8, 9, 10). Each isoform binds to the substrates with different affinities, suggesting, in vivo, a substrate specific regulation of the signaling pathways by the different JNK isoforms.

In a recent publication of Xie X et al, (*Structure* 1998, 6 (8); 983-991) it has been suggested that activation of stress-activated signal transduction pathways are required for neuronal apoptosis induced by NGF withdrawal in rat PC-12 and superior cervical ganglia (SCG) sympathetic neuronal cells. Inhibition of specific kinases, namely MAP kinase kinase 3 (MKK3) and MAP kinase kinase 4 (MKK4), or c-Jun (part of the MKK-4 cascade) may be sufficient to block apoptosis (see also Kumagae Y et al, in *Brain Res Mol Brain Res,* 1999, 67(1), 10-17 and Yang DD et al in *Nature,* 1997, 389 (6653); 865-870). Within a few hours of NGF deprivation in SCG neurones, c-Jun becomes highly phosphorylated and protein levels increase. Similarly in rat PC-12 cells deprived of NGF, JNK and p38 undergo sustained activation while ERKs are inhibited. Consistent with this JNK3 KO mice are resistant to excitotoxicity induced apoptosis in the hippo-campus and more importantly they display greatly reduced epileptic like seizures in response to excitotoxicity as compared to normal animals (*Nature* 1997, 389, 865-870). More recently, it has been reported that the JNK signalling pathway is implicated in cell proliferation and could play an important role in autoimmune diseases (*Immunity,* 1998, 9, 575-585; *Current Biology,* 1999, 3, 116-125) which are mediated by T-cell activation and proliferation.

Naive (precursor) $CD4^+$ helper T (Th) cells recognise specific MHC-peptide complexes on antigen-presenting cells (APC) via the T-cell receptor (TCR) complex. In addition to the TCT-mediated signal, a co-stimulatory signal is provided at least partially by the ligation of CD28 expressed on T-cells with B7 proteins on APC. The combination of these two signals induces T-cell clonal expression.

After 4-5 days of proliferation, precursor of $CD4^+$ T cells differentiate into armed effector Th cells that mediate the functions of the immune system. During the differentiation process, substantial reprogramming of gene expression occurs.

Two subsets of effector Th cells have been defined on the basis of their distinct cytokine secretion pattern and their immuno-modulatory effects: Th1 cells produce IFN γ and LT (TNF-β), which are required for cell-mediated inflammatory reactions; Th2 cells secrete IL-4, IL-5, IL-6, IL-10 and IL-13, which mediate B cell activation and differentiation. These cells play a central role in the immune response. The JNK MAP Kinase pathway is induced in Th1 but not in Th2 effector cells upon antigen stimulation. Furthermore, the differentiation of precursor $CD4^+$ T cells into effector Th1 but not Th2 cells is impaired in JNK2-deficient mice. Therefore, in recent years it has been realised that the JNK kinase pathway plays an important role in the balance of Th1 and Th2 immune response through JNK2.

Some transcription factors known to be JNK substrates are the Jun proteins (c-jun, JunB and Jun D), the related transcription factors ATF2 and ATFa, Ets transcription factors such as Elk-1 and Sap-1, the tumor suppressor p53 and a cell death domain protein (DENN).

Activation of the JNK pathway has been documented in a number of disease processes, thus providing a rationale for targeting this pathway for drug discovery. In addition, molecular genetic approaches have validated the pathogenic role of this pathway in several diseases.

For example, auto-immune and inflammatory diseases derive from the inappropriate activation of the immune system. Activated immune cells express many genes encoding inflammatory molecules, including cytokines, growth factors, cell surface receptors, cell adhesion molecules and degradative enzymes. Many of these genes are known to be regulated by the JNK pathway, through the activation of the transcription factors c-Jun and ATF-2.

The inhibition of JNK activation in bacterial lipopolysaccharide-stimulated macro-phages, effectively modulates the production of the key pro-inflammatory cytokine, TNFα (11).

The inhibition of JNK activation decreases the transcription factor activation responsible of the inducible expression of matrix metalloproteinases (MMPs) (12), which are known to be responsible of the promotion of cartilage and bone erosion in rheumatoid arthritis and of generalized tissue destruction in other auto-immune diseases.

The JNK cascade is also activated in T cells by antigen stimulation and CD28 receptor co-stimulation (13) and regulates the production of the IL-2 promoter (14). Inappropriate activation of T lymphocytes initiates and perpetuates many auto-immune diseases, including asthma, inflammatory bowel syndrome and multiple sclerosis.

In neurons vulnerable to damage from Alzheimer's disease and in CA1 neurons of patients with acute hypoxia (15), JNK3 protein is highly expressed. The JNK3 gene was also found to be expressed in the damaged regions of the brains of Alzheimer's patients (16). In addition, neurons from JNK3 KO mice were found to become resistant to kainic acid induced neuronal apoptosis compared to neurons from wildtype mice (8).

Based on these findings, the JNK signaling pathway and especially that of JNK2 and JNK3, is thought to be implicated in apoptosis-driven neurodegenerative diseases such as Alzheimer's disease, Parkinson's disease, epilepsy and seizures, Huntington's disease, traumatic brain injuries as well as ischemic and hemorrhaging strokes.

Cardiovascular diseases, such as atherosclerosis and restenosis result from defective regulation of growth of the blood vessel wall. The JNK pathway is activated by atherogenic stimuli and regulates local cytokine and growth factor production in vascular cells (17, 18) inducing pro-atherosclerotic gene (19).

Ischemia alone or coupled with reperfusion in the heart, liver, kidney or brain results in cell death and scar formation, which can ultimately lead to congestive heart failure, hepatic disorders, renal failure or cerebral dysfunction. The JNK pathway is activated by ischemia and reperfusion in the heart (20), leading to the activation of JNK-responsive genes and leukocyte-Mediated tissue damage. JNK activation is also observed in kidney (21) or liver (22) following ischemia and reperfusion. The down-regulation of JNKs has been proven to improve renal function and long-term outcome during nephritic and ischemic renal failure (23).

Cancer is characterized by uncontrolled growth, proliferation and migration of cells. In early lung cancer, expression of c-jun is altered and may mediate growth factor signaling in non-small cell lung cancer (24). In addition to regulating c-jun production and activity, JNK activation can regulate phosphorylation of p53, and thus can modulate cell cycle progression (25). Moreover, the role of JNK activation in HTLV-1 (human T cell leukemia virus type 1) mediated tumorgenesis (26) suggests the potential use of JNK inhibitors in cancer treatment (27). Selective inhibition of JNK activation by a naturally occurring JNK inhibitory protein, called JNK-interacting-protein-1 (JIP1), blocks cellular transformation (28). Thus, JNK inhibitors may block transformation and tumor cell growth.

With the objective of inhibiting the JNK kinase pathway, WO/9849188 teaches the use of a human polypeptide, i.e.

JNK-interacting protein 1 (JIP-1), which is a biological product and which has also been assayed for overcoming apoptosis related disorders.

Although such human polypeptides have been confirmed to have an inhibitory effect onto the JNK kinase pathway, a whole variety of drawbacks are associated with their use:

Active bio-peptides or bio-proteins are only obtained by means of rather comprehensive and expensive bio-synthesis which consequently frequently renders the resulting products fairly cost-intensive.

The peptides are known to display poor membrane penetration and may not cross the blood brain membrane, The principal drawback to the use of peptide inhibitors or antagonists is the problem of low oral bioavailability resulting from intestinal degradation. Hence, they must be administered parenterally and finally, peptide inhibitors or antagonists are frequently viewed by the host body as intruding material to be eliminated, thus setting off an auto-immune response.

The high relevance of the JNK pathway in some widely spread diseases stresses the need to develop inhibitors, preferentially selective, of JNKs.

It is therefore an objective of the present invention to provide molecules which are suitable for the treatment of a variety of diseases, in particular of neuronal or the autoimmune system related disorders, cancer, ischemic conditions and cardiovascular diseases.

It is notably an objective of the present invention to provide chemical compounds which are able to modulate, preferably to down-regulate or to inhibit the JNK (Jun kinase) pathway so to be useful in method of treating diseases which involve the JNK pathway. Moreover, it is an objective of the present invention to provide methods for preparing said chemical compounds. It is furthermore an objective of the present invention to provide a new category of pharmaceutical formulations for the treatment of diseases, in particular those mediated by the JNK function.

It is finally an objective of the present invention to provide a method for the treatment and/or prevention of diseases that are caused by disorders of the autoimmune and/or the neuronal system.

DESCRIPTION OF THE INVENTION

The aforementioned objectives have been met according to the independent claims. Preferred embodiments are set out within the dependent claims which are incorporated herewith.

The following paragraphs provide definitions of the various chemical moieties that make up the compounds according to the invention and are intended to apply uniformly throughout the specification and claims unless an otherwise expressly set out definition provides a broader definition.

"$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like.

"Aryl" refers to an unsaturated aromatic carbocyclic group of from 6 to 14 carbon atoms having a single ring (e.g. phenyl) or multiple condensed rings (e.g. naphthyl). Preferred aryl include phenyl, naphthyl, phenantrenyl and the like.

"$C_1$-$C_6$-alkyl aryl" refers to $C_1$-$C_6$-alkyl groups having an aryl substituent, including benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetra-hydroisoquinolyl, purinyl, pteridinyl, carbazolyl, xanthenyl or benzoquinolyl. "$C_1$-$C_6$-alkyl heteroaryl" refers to $C_1$-$C_6$-alkyl groups having a heteroaryl substituent, including 2-furylmethyl, 2-thienylmethyl, 2-(1H-indol-3-yl)ethyl and the like.

"Alkenyl" refers to alkenyl groups preferably having from 2 to 6 carbon atoms and having at least 1 or 2 sites of alkenyl unsaturation. Preferable alkenyl groups include ethenyl (—CH=CH$_2$), n-2-propenyl (allyl, —CH$_2$CH=CH$_2$) and the like.

"Alkynyl" refers to alkynyl groups preferably having from 2 to 6 carbon atoms and having at least 1-2 sites of alkynyl unsaturation, preferred alkynyl groups include ethynyl (—C≡CH), propargyl (—CH$_2$C≡CH), and the like.

"Acyl" refers to the group —C(O)R where R includes "$C_1$-$C_6$-alkyl", "aryl", "heteroaryl", "$C_1$-$C_6$-alkyl aryl" or "$C_1$-$C_6$-alkyl heteroaryl".

"Acyloxy" refers to the group —OC(O)R where R includes "$C_1$-$C_6$-alkyl", "aryl", "heteroaryl", "$C_1$-$C_6$-alkyl aryl" or "$C_1$-$C_6$-alkyl heteroaryl".

"Alkoxy" refers to the group —O—R where R includes "$C_1$-$C_6$-alkyl" or "aryl" or "heteroaryl" or "$C_1$-$C_6$-alkyl aryl" or "$C_1$-$C_6$-alkyl heteroaryl". Preferred alkoxy groups include by way of example, methoxy, ethoxy, phenoxy and the like.

"Alkoxycarbonyl" refers to the group —C(O)OR where R includes "$C_1$-$C_6$-alkyl" or "aryl" or "heteroaryl" or "$C_1$-$C_6$-alkyl aryl" or "$C_1$-$C_6$-alkyl heteroaryl".

"Aminocarbonyl" refers to the group —C(O)NRR' where each R, R' includes independently hydrogen or $C_1$-$C_6$-alkyl or aryl or heteroaryl or "$C_1$-$C_6$-alkyl aryl" or "$C_1$-$C_6$-alkyl heteroaryl".

"Acylamino" refers to the group —NR(CO)R' where each R, R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl".

"Halogen" refers to fluoro, chloro, bromo and iodo atoms.

"Sulfonyl" refers to group "—SO$_2$—R" wherein R is selected from H, "aryl", "heteroaryl", "$C_1$-$C_6$-alkyl", "$C_1$-$C_6$-alkyl" substituted with halogens e.g. an —SO$_2$—CF$_3$ group, "$C_1$-$C_6$-alkyl aryl" or "$C_1$-$C_6$-alkyl heteroaryl".

"Sulfoxy" refers to a group "—S(O)—R" wherein R is selected from H, "$C_1$-$C_6$-alkyl", "$C_1$-$C_6$-alkyl" substituted with halogens e.g. an —SO—CF$_3$ group, "aryl", "heteroaryl", "$C_1$-$C_6$-alkyl aryl" or "$C_1$-$C_6$-alkyl heteroaryl".

"Thioalkoxy" refers to groups —S—R where R includes "$C_1$-$C_6$-alkyl" or "aryl" or "heteroaryl" or "$C_1$-$C_6$-alkyl aryl" or "$C_1$-$C_6$-alkyl heteroaryl". Preferred thioalkoxy groups include thiomethoxy, thioethoxy, and the like.

"Substituted or unsubstituted": Unless otherwise constrained by the definition of the individual substituent, the above set out groups, like "alkyl", "alkenyl", "alkynyl", "aryl" and "heteroaryl" etc. groups can optionally be substituted with from 1 to 5 substituents selected from the group consisting of "$C_1$-$C_6$-alkyl", "$C_1$-$C_6$-alkyl aryl", "$C_1$-$C_6$-alkyl heteroaryl", "$C_2$-$C_6$-alkenyl", "$C_2$-$C_6$-alkynyl", primary, secondary or tertiary amino groups or quarter-nary ammonium moieties, "acyl", "acyloxy", "acylamino", "aminocarbonyl", "alkoxycarbonyl", "aryl", "heteroaryl", carboxyl, cyano, halogen, hydroxy, mercapto, nitro, sulfoxy, sulfonyl, alkoxy, thioalkoxy, trihalomethyl and the like. Alternatively said substitution could also comprise situations where neighboring substituents have undergone ring closure, notably when viccinal functional substituents are involved, thus forming e.g. lactams, lactons, cyclic anhydrides, but also acetals, thioacetals, aminals formed by ring closure for instance in an effort to obtain a protective group.

"Pharmaceutically acceptable salts or complexes" refers to salts or complexes of the below-identified compounds of formula I that retain the desired biological activity. Examples of such salts include, but are not restricted to acid addition salts formed with inorganic acids (e.g. hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and polygalacturonic acid. Said compounds can also be administered as pharmaceutically acceptable quaternary salts known by a person skilled in the art, which specifically include the quarternary ammonium salt of the formula —NR,R',R''+Z−, wherein R, R', R'' is independently hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

"Pharmaceutically active derivative" refers to any compound that upon administration to the recipient, is capable of providing directly or indirectly, the activity disclosed herein.

"Ionisable moiety" refers to functional groups, wherein its characteristic electron distribution confers to said moiety its capacity to be transformed into an ionic or ionised group, or in other words into a salt. Preferred ionisable moieties are basic groups like amines that are protonated thus yielding a salt.

"Lipophilic chain" refers to groups which have a pronounced attraction to hydrophobic groups, substituents or compounds, notably to lipids or fatty compounds or moieties. They notably include optionally substituted $C_4$-$C_{18}$-alkyl groups.

"Hydrophilic group" refers to functional groups which have a pronounced attraction to hydrophilic or polar groups, substituents or compounds. or fatty compounds or moieties. They notably include hydroxides, sulfates or sulfonates or amines or ammonium salts.

"Enantiomeric excess" (ee) refers to the products that are obtained by an essentially enantiomeric synthesis or a synthesis comprising an enantioselective step, whereby a surplus of one enantiomer in the order of at least about 52% ee is yielded. In the absence of an enantiomeric synthesis, racemic products are usually obtained that do however also have the inventive set out activity as JunK inhibitors.

One aspect of the present invention are the novel benzsulfonamide derivatives according to formula I. Such compounds are suitable pharmaceutically active agents, by effectively modulating, in particular by down-regulating inhibiting the action of JNK's, notably of JNK 2 and/or 3.

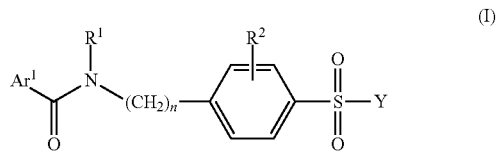

(I)

The compounds of formula I according to the present invention being suitable pharmaceutical agents are those wherein $Ar^1$ is a substituted or unsubstituted aryl or heteroaryl group.

X is O or S, preferably O.

$R^1$ is hydrogen or a $C_1$-$C_6$-alkyl group, preferably H $R^2$ is hydrogen, —$COOR^3$, —$CONR^3R^{3'}$, OH, a $C_1$-$C_4$ alkyl substituted with an OH group, a hydrazido carbonyl group, a sulfate, a sulfonate, an amine or an ammonium salt.

n is either 0 or 1, preferably 1

Y is a piperidine or piperazine moiety according to the below formulae

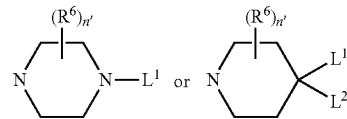

In said piperidine or piperazine groups, $L^1$ and $L^2$ are independently selected from each other from the group consisting of H, $C_1$-$C_6$-alkyl, $C_2$-$C_6$-alkenyl, $C_2$-$C_6$-alkynyl, $C_4$-$C_8$-cycloalkyl optionally containing 1-3 heteroatoms and optionally fused with aryl or heteroaryl; or $L^1$ and $L^2$ are independently selected from the group consisting of aryl, heteroaryl, aryl-$C_1$-$C_6$-alkyl, heteroaryl-$C_1$-$C_6$-alkyl, —C(O)—$OR^3$, —C(O)—$R^3$, —C(O)—$NR^3R^3$, —$NR^3R^3$, —$NR^{3'}C(O)R^3$, —$NR^{3'}C(O)NR^3R^3$, —(SO)$R^3$, —(SO$_2$)$R^3$, —NHSO$_2R^3$, and —SO$_2$NR$^{3'}R^3$.

$R^3$, $R^{3'}$ are independently selected from the group consisting of H, $C_1$-$C_6$-alkyl, $C_2$-$C_6$-alkenyl, aryl, heteroaryl, aryl-$C_1$-$C_6$-alkyl, heteroaryl-$C_1$-$C_6$-alkyl;

Alternatively, $L^1$ and $L^2$ taken together form a 4-8-membered, saturated cyclic alkyl or heteroalkyl group.

$R^6$ is selected from the group consisting of hydrogen, $C_1$-$C_6$-alkyl, $C_1$-$C_6$-alkoxy, OH, halogen, nitro, cyano, sulfonyl, oxo (=O). n' is an integer from 0 to 4, preferably 0.

Y may also be a pyrrolidine, an azepan or a 1,4-diazepan moiety of the below formulae

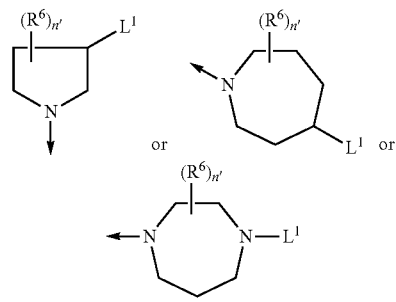

whereby $L^1$, $R^6$ and n' are as above defined.

All of the above mentioned aryl or heteroaryl groups may optionally be substituted by at least one of the groups selected from $C_1$-$C_6$-alkyl, like trihalomethyl, $C_1$-$C_6$-alkoxy, acyloxy, $C_2$-$C_6$-alkenyl, $C_2$-$C_6$-alkynyl, amino, acylamino, aminocarbonyl, $C_1$-$C_6$-alkoxycarbonyl, aryl, carboxyl, cyano, halogen, hydroxy, nitro, sulfonyl, sulfoxy, $C_1$-$C_6$-thioalkoxy.

The present invention also includes the geometrical isomers, the optical active forms, enantiomers, diastereomers of compounds according to formula I, as well as their racemates and also pharmaceutically acceptable salts as well as the pharmaceutically active derivatives of the benzsulfonamide derivatives of formula I.

Preferred $Ar^1$ in formula I are those that are independently selected from the group consisting of phenyl, thienyl, furyl, pyridyl, optionally substituted by $C_1$-$C_6$-alkyl, like tri-halomethyl, $C_1$-$C_6$-alkoxy, $C_2$-$C_6$-alkenyl, $C_2$-$C_6$-alkynyl, amino, acylamino, aminocarbonyl, $C_1$-$C_6$-alkoxycarbonyl, aryl, carboxyl, cyano, halo, hydroxy, nitro, sulfonyl, sulfoxy, acyloxy, $C_1$-$C_6$-thioalkoxy. The most preferred $Ar^1$ is a substituted phenyl, including halophenyl, e.g. a 4-chlorophenyl, nitrophenyl, hydroxyphenyl, alkoxy phenyl, pyridyl, 3,4,-dihydroxyphenyl, thioxo-dihydropyridine or its tautomer, pyrazole.

Where $Ar^1$ is a 4-chlorophenyl, nitrophenyl, hydroxyphenyl, alkoxy phenyl, pyridyl, 3,4,-dihydroxyphenyl, thioxo-dihydropyridine or its tautomer, pyrazole group, X is preferably O, $R^1$ is hydrogen, n is 1.

A particularly preferred embodiment of the present invention is related to the sulfonamide derivatives, wherein Y is a substituted or unsubstituted piperidine residue,

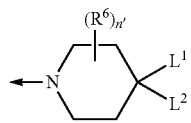

whereby $R^6$, n', $L^1$ and $L^2$ are as above defined.

$R^6$ is H, $L^2$ is H, $L^1$ is an ionisable moiety to which a lipophilic chain is attached.

Such ionisable moiety $L^1$ to which a lipophilic chain is attached are is —$NHR^3$; whereby $R^3$ is a straight or branched $C_4$-$C_{12}$-alkyl, preferably a $C_6$-$C_{10}$-alkyl, optionally substituted with a cyclohexyl group, or $R^3$ is a benzyl group.

Alternatively, Y may be

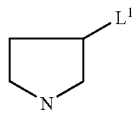

wherein $L^1$ is as above defined, but is preferably is an ionisable moiety to which a lipophilic chain is attached. Such an ionisable moiety could be an amino group which is substituted with a lipophilic $C_1$-$C_{12}$ alkyl, preferably $C_4$-$C_6$ alkyl, or a substituted or unsubstituted aryl group, preferably the substituted aryl group is a trifluoromethylsulfonyl phenyl.

The above set out ionisable moieties within $L^1$ are actually hydrophilic groups, thus conferring a better solubility to the molecules of formula I. The improvement of the solubility of the molecules of formula I through an ionisable moiety within $L^1$ is of particular of interest notably for pharmaceutical compounds. The most preferred ionisable moiety is the secondary amino moiety. Particularly potent compounds of formula I in respect of the inhibition of JunKinases are those where $L^1$ also comprises a lipophilic moiety. Most preferred is a $C_4$-$C_6$ alkyl group attached to an ionisable moiety like an amino group. Such lipophilic groups are believed to enter into a cavity of the enzyme to be inhibited.

Specific examples of compounds of formula I include the following:
4-chloro-N-(3-{[4-(hexylamino)-1-piperidinyl]
  sulfonyl}phenyl)benzamide
4-chloro-N-{4-[(4-{[4-(trifluoromethyl)benzyl]amino}-1-
  piperidinyl)sulfonyl]phenyl}benzamide
4-chloro-N-(4-{[4-({2-[3-(trifluoromethyl)phenyl]
  ethyl}amino)-1-piperidinyl]sulfonyl}phenyl)benzamide
4-chloro-N-(4-{[4-(hexylamino)-1-piperidinyl]
  sulfonyl}benzyl)benzamide
4-chloro-N-(4-{[4-(hexylamino)-1-piperidinyl]
  sulfonyl}phenyl)benzamide
4-chloro-N-(3-{[4-(hexylamino)-1-piperidinyl]
  sulfonyl}benzyl)benzamide
4-chloro-N-{3-[(4-{[4-(trifluoromethyl)benzyl]amino}-1-
  piperidinyl)sulfonyl]benzyl}benzamide
4-chloro-N-(3-{[4-({2-[3-(trifluoromethyl)phenyl]
  ethyl}amino)-1-piperidinyl]sulfonyl}benzyl)benzamide
4-chloro-N-(4-{[4-({2-[3-(trifluoromethyl)phenyl]
  ethyl}amino)-1-piperidinyl]sulfonyl}benzyl)benzamide
4-chloro-N-(3-{[3-(hexylamino)-1-pyrrolidinyl]
  sulfonyl}phenyl)benzamide
4-chloro-N-{4-[(4-{[4-(trifluoromethyl)benzyl]amino}-1-
  piperidinyl)sulfonyl]benzyl}benzamide
4-chloro-N-(3-{[3-({2-[3-(trifluoromethyl)phenyl]
  ethyl}amino)-1-pyrrolidinyl]sulfonyl}phenyl)benzamide
N-(4-{[4-(butylamino)-1-piperidinyl]sulfonyl}benzyl)-2-
  oxo-1,2-dihydro-3-pyridinecarboxamide
4-chloro-N-{4-[(3-{[4-(trifluoromethyl)benzyl]amino}-1-
  pyrrolidinyl)sulfonyl]phenyl}benzamide
4-chloro-N-{4-[(3-{[2-[3-(trifluoromethyl)phenyl]
  ethyl}amino)}-1-pyrrolidinyl)sulfonyl]
  phenyl}benzamide
4-chloro-N-{3-[(4-{[4-(trifluoromethyl)benzyl]amino}-1-
  piperidinyl)sulfonyl]phenyl}benzamide
4-chloro-N-{3-[(4-{3-[(trifluoromethyl)sulfonyl]anilino}-
  1-piperidinyl)sulfonyl]phenyl}benzamide
4-chloro-N-(4-{[3-hexylamino)-1-pyrrolidinyl]
  sulfonyl}phenyl)benzamide
4-chloro-N-{4-[(4-{3-[(trifluoromethyl)sulfonyl]anilino}-
  1-piperidinyl)sulfonyl]benzyl}benzamide
4-chloro-N-(4-{[3-({2-[3-(trifluoromethyl)phenyl]
  ethyl}amino)-1-pyrrolidinyl]sulfonyl}phenyl)benzamide
N-{3-[(4-anilino-1-piperidinyl)sulfonyl]phenyl}-4-chlorobenzamide
4-chloro-N-(3-{[4-({2-[3-(trifluoromethyl)phenyl]
  ethyl}amino)-1-piperidinyl]sulfonyl}phenyl)benzamide
4-chloro-N-(4-{[3-({2-[3-(trifluoromethyl)phenyl]
  ethyl}amino)-1-pyrrolidinyl]sulfonyl}phenyl)benzamide
4-chloro-N-{3-[(4-{3-[(trifluoromethyl)sulfonyl]anilino)
  -1-piperidinyl)sulfonyl]benzyl}benzamide
4-chloro-N-{4-[(4-{3-[(trifluoromethyl)sulfonyl]anilino}-
  1-piperidinyl)sulfonyl]phenyl}benzamide
4-chloro-N-{3-[(3-{[4-(trifluoromethyl)benzyl]amino}-1-
  pyrrolidinyl)sulfonyl]benzyl}benzamide
4-chloro-N-(4-{[3-({2-[3-(trifluoromethyl)phenyl]
  ethyl}amino)-1-pyrrolidinyl]sulfonyl}benzyl)benzamide
N-(4-{[4-(hexylamino)-1-piperidinyl]sulfonyl}benzyl)-2-
  hydroxynicotinamide
N-(3-{[4-(hexylamino)-1-piperidinyl]sulfonyl}benzyl)-2-
  hydroxynicotinamide
2-hydroxy-N-{3-[(4-{3-[(trifluoromethyl)sulfonyl]anilino}-
  1-piperidinyl)sulfonyl]benzyl}nicotinamide 2-hydroxy-N-{4-[(4-{3-[(trifluoromethyl)sulfonyl]anilino}-1-piperidinyl)sulfonyl]benzyl}nicotinamide The compounds of formula I are suitable for use in treating disorders of the immune system and neuronal system of mammals, notably of human beings. Such neuronal system disorders include for example neurodegenerative diseases e.g. Alzheimer's disease, Huntington's disease, Parkinson's disease, retinal diseases, spinal cord injury, multiple sclerosis, head trauma, epilepsy and seizures, ischemic and hemorragic brain strokes. Immune system disorders include for example asthma, transplant rejection, inflammatory processes such as inflammatory bowel disease (IBD), cartilage and bone erosion disorders, rheumatoid arthritis, septic shock.

The compounds according to formula I are also suitable for use in treating cancers, such as breast, colorectal, pancreatic, prostate, testicular, ovarian, lung, liver and kidney cancers.

In another embodiment, the compounds according to formula I may be used for treating cardiovascular diseases including atherosclerosis, restenosis, stroke, ischemia, e.g. cerebral ischemia, myocardial infarction.

In another embodiment, the compounds according to formula I may be used for treating various ischemic conditions including heart and kidney failures, hepatic disorders and brain reperfusion injuries.

Preferably, the compounds according to formula I, alone or in the form of a pharmaceutical composition, are useful for the modulation of the JNK pathway, more specifically for treatment or prevention of disorders associated with expression or activity of JNK, notably of JNK2 and -3. Said modulation usually preferably involves the inhibition of the JNK pathways, notably of the JNK2 and/or -3. Such an abnormal expression or activity of JNK may be triggered by numerous stimuli (e.g. stress, septic shock, oxidative stress, cytokines) and may cause a cascade of processes, leading to, for example, uncontrolled apoptosis, inflammatory responses or oncogenic processes. These phenomena are frequently involved in various disorders including the above enumerated disorders and disease states. Hence, the compounds according to the invention may be used for the treatment of disorders by modulating the JNK function or signaling pathways. The modulation of the JNK function or pathways may involve its activation, but preferably it involves the down-regulation up to inhibition of the JNK pathways, notably of JNK1 and/or -2 and/or JNK3. The compounds of the invention may be employed alone or in combination with further pharmaceutical agents, e.g. with a further JNK modulator.

Still a further object of the present invention is a process for preparing the novel sulfamide derivatives according to formula I which have been set out above.

The benzsulfonamide derivatives of this invention can be prepared from readily available starting materials using the following general methods and procedures.

It will be appreciated that where typical or preferred experimental conditions (i.e., reaction temperatures, time, moles of reagents, solvents, etc.) are given, other experimental conditions can also be used unless otherwise stated. Optimum reaction conditions may vary with the particular reactants or solvent used, but such conditions can be determined by one skilled in the art by routine optimisation procedures.

The compounds of formula I may generally be obtained by either of the approaches set out in Scheme 1 or 2:

Scheme 1

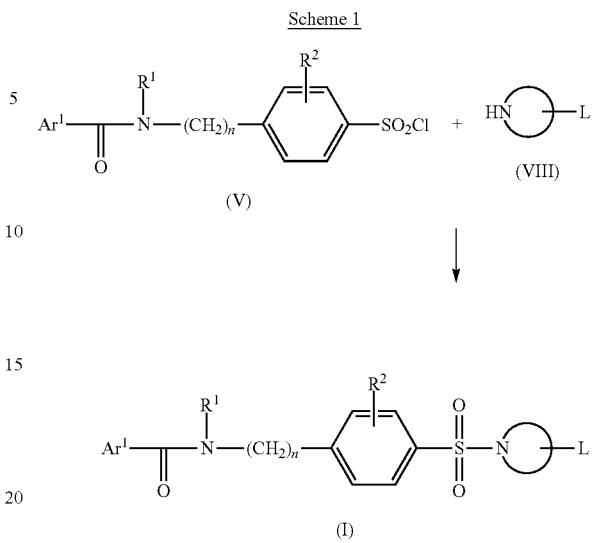

Scheme 2

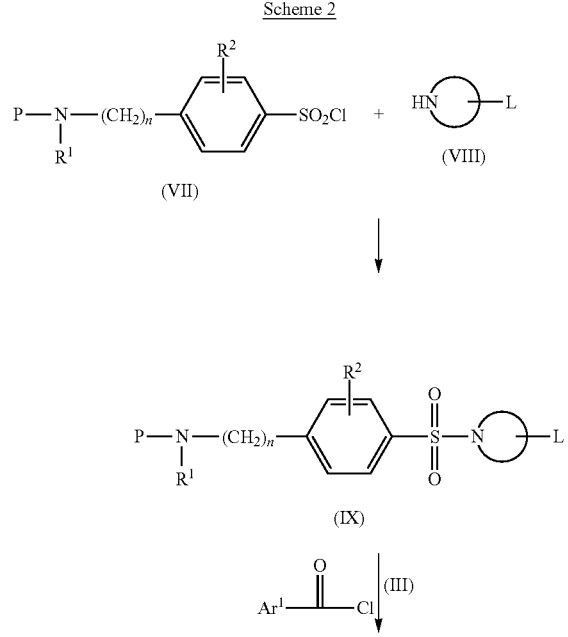

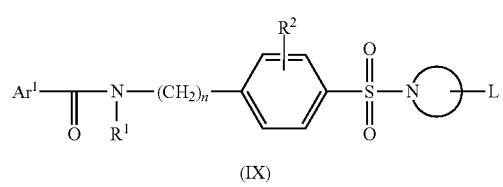

Thereby, $Ar^1$, $R^1$, $R^2$, L and n are as above defined, P is a suitable protective group ($R^1$ is preferably not a hydrogen, preferably a suitable protective group).

Sulfonyl chlorides of formula (V), as used in Scheme 1, may be prepared according to a procedure set out in Scheme 3:

Scheme 3:

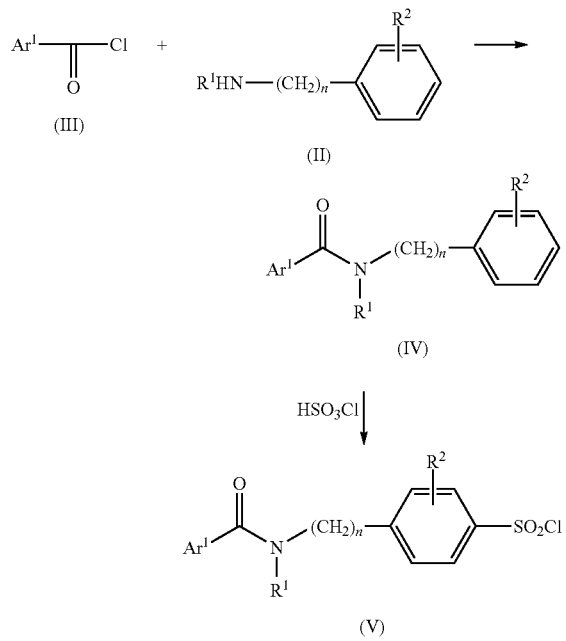

Thereby, $Ar^1$, $R^1$, $R^2$, L and n are as above defined.

Amines of formula II are either known compounds or may be prepared from known compounds by conventional procedures. Preferred amines as starting materials include aniline and benzomethylamine.

The acyl chlorides of formula III are also commercially available or previously described compounds. Preferred acyl chlorides include halogenobenzoylchlorides, e.g. 4-chlorobenzoyl chloride, 4-fluorobenzoyl chloride or trifluoromethylbenzoyl chloride, alkoxybenzoylchloride, pyridylcarbonylchloride and the like. Acyl halides (III) may also be prepared by reacting the corresponding carboxylic acid with an inorganic acid halide, such as thionyl chloride, phosphorus trichloride or oxalyl chloride under conventional conditions. Generally, such reaction is performed upon using about 1 to 5 molar equivalents of the inorganic acyl halide or oxalyl chloride, either in pure form or in an inert solvent, such as carbon tetrachloride, at temperature in the range of about 0° C. to about 80° C. for about 1 to about 48 hours. A catalyst, as N,N-dimethylformamide, may also be used in this reaction.

When an acyl halide (III) is employed in the coupling reaction set out in Scheme 3, it is typically reacted with amine (II) in the presence of a suitable base to scavenge the acid generated during the reaction. Suitable bases include, by way of example, triethylamine, diisopropylethylamine, N-methylnorpholine and the like. Alternatively, an excess of amine II may be used to scavenge the acid generated during the reaction.

Alternatively, the carboxylic acid of compound (III) can be employed in the coupling reaction. The carboxylic acids and derivatives (III) are usually commercially available reagents or can be prepared by conventional procedures.

The coupling reaction of carboxylic acid of formula III (i.e. the acyl chloride) with the amine (II) is typically performed while using any conventional coupling reagent including, for example, carbodiimides such as dicyclohexylcarbodiimide, N-(3-dimethylaminopropyl)-N'-ethylcarbodiimide and other promoting agents, such as N, N-carbonyl-diimidazole or PyBOP. This reaction can be conducted with or without the use of well known additives such as N-hydroxysuccinimide, 1-hydroxybenzotriazole, etc. which are known to facilitate the coupling of carboxylic acids and amines.

The coupling reaction using either acyl halide (III) or its carboxylic acid is preferably conducted at a temperature of from about 0° C. to about 6° C. for about 1 to about 24 hours. Typically, the reaction is conducted in an inert aprotic polar solvent such as N, N-dimethylformamide, dichloromethane, chloroform, acetonitrile, tetrahydrofuran and the like using about 1 to about 5 molar equivalents of the amine based on the carboxylic acid or its acid halide. Upon completion of the reaction, the carboxamide (IV) is recovered by conventional methods including precipitation, chromatography, filtration, distillation and the like.

The sulfonyl chlorides of formula V necessary for the preparation of the final products of formula I, notably those being sulfonylpiperidines or -pyrrolidines or -azepans, are pre-pared using conventional sulfonating methods applied on the carboxamides (IV):

A preferred sulfonating reagent for use in this reaction (as set out in scheme 3) is chlorosulfonic acid ($HSO_3$—Cl). Typically, the sulfonation reaction is performed by treating the carboxamide of formula (IV) with about 5 to about 10 molar equivalent of the sulfonating reagent in an inert solvent, such as dichloromethane, at a temperature ranging from about −70° C. to about 50° C. Preferably, the addition of chlorosulfonic acid takes place at −70° C. and leads to the formation of the intermediate sulfonic acid. Increasing the temperature to 20° C. allows the formation of the sulfonyl chloride of formula V.

Compounds of formula I with X=S are accessible from the corresponding arylamides (with X=O), e.g. benzamides, through standard functional group inter-conversion methods well known to the person skilled in the art, e.g., by treatment with Lawesson's reagent or others (Pedersen, B. S. et al.; *Bull. Soc. Chim. Belg.* 1978, 87, 223).

An alternative approach for the preparation of compounds of formula I is set out in Scheme 2 above and involves the following steps:

Protection of the amine function of compounds of formula II;
Chlorosulfonylation of the benzo group, thus yielding compounds of formula VII;
Formation of the sulfonamide function (yielding compounds IX);
Removal of the protecting group P (Deprotection) within compounds IX;
Acylation of the above generated free amine to provide compounds (I);

Thereby, the sulfonyl chloride precursor (VII) may be prepared by the following steps:

Scheme 4

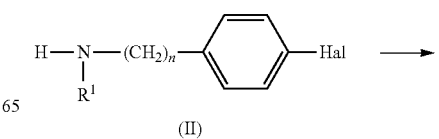

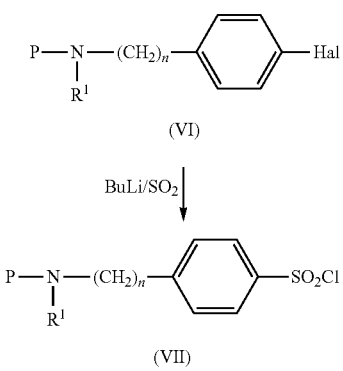

(VI)

BuLi/SO₂ ↓

P—N(R¹)—(CH₂)ₙ—C₆H₄—SO₂Cl (VII)

Amines of formula II are protected with a suitable protecting group for an amine moiety to provide intermediate of formula VI wherein P denotes the protecting group. Numerous protecting groups P of the amine function as well as their introduction and removal, are well described in T. W. Greene and G. M. Wuts, Protecting groups in Organic Synthesis, Third Edition, Wiley, New York, 1998, and references cited therein. Preferred are protecting groups that are acids and bases stable and can be further removed by using metal transition complexes such as palladium complexes, for example the allylcarbamate group (Alloc) or the N,N'-bisallyl group. Another preferred protecting group is the maleimide group which is stable in a all range of experimental conditions.

The introduction of said groups may be performed by reacting the corresponding bisallylcarbonate anhydride or allylbromide or maleic anhydride in the presence of a base such as triethylamine, diisopropylethylamine, N-methylmorpholine and the like in an aprotic solvent such as N,N-dimethylformamide, dichloromethane, chloroform, acetonitrile, tetrahydrofuran and the like at a temperature ranging from about 0° C. to about 80° C.

Compounds of formula VI in Scheme 4 are then sulfonated using a conventional, very mild sulfonating procedure that allows the obtention of sulfonyl chloride of formula VII. Typically, protected amines VI are treated with a base such as n-butyllithium or tert-butyl-lithium under an inert atmosphere, in a polar aprotic solvent such as tetrahydrofuran, ether or dioxane at a temperature ranging from −70° C. to 0° C. during a time ranging from 15 minutes to 4 hours. The so formed anion is then treated with SO₂Cl₂ or most preferably SO₂ by bubbling the gas into the reaction mixture at a temperature ranging from −70° C. to 20° C. during a time ranging from 5 minutes to 1 hour. The sulfonate obtained is then transformed "in situ" to the sulfonyl chloride of formula VII by contacting with N-chlorosuccinimide at a temperature ranging from 0° C. to 70° C.

Following either of Schemes 1 and 2, the sulfonamide derivatives of formula I may be obtained by reacting sulfonyl chlorides V or VII with a cyclic or bicyclic amine (VIII), i.e. an alkyl containing a nitrogen according to the above definition. Preferred cyclic amines (VIII) include pyrrolidine or azepan or piperidine derivatives of the general formula (VIII") or (VIII') or (VIII''').

whereby $(R^6)_{n'}$, $L^1$ and $L^2$ are as above defined.

The amines of formula VIII''' or VIII" or VIII' are either commercially available compounds or compounds that may be prepared by known procedures.

The coupling reaction of sulfonyl chlorides (V) and (VII) with the amines VIII to provide sulfonamides of formula I is performed by contacting the sulfonyl chlorides with an amine of formula VIII in the presence of a suitable base to scavenge the acid generated during the reaction. Suitable bases include, by way of examples, triethylamine, diisopropylethylamine, N-methylmorpholine and the like. The reaction is preferably conducted in a solvent such as N,N-dimethylformamide, dimethylsulfoxide, N-methyl-pyrrolidone, ethanol, acetonitrile typically at a temperature from about 0° to about 100° C.

According to a preferred embodiment, the sulfonamide derivatives of formula I are pre-pared by reacting a sulfonyl chloride V or VII, with a piperidine of formula VIII'''.

Piperidines of formula VIII''' are either commercially available or they may be pre-pared by known procedures. Such conventional methods known by one skilled in the art are described by way of examples in *J Pharm. Sci.* 1972, 61, 1316; *J. Heterocyclic. Chem.*, 1986, 23, 73; *Tetrahedron Lett.*, 1996, 37, 1297, U.S. Pat. No. 5,106,983, WO/9113872 and WO/9606609.

The piperidino sulfonamides of formula I may be prepared by contacting the sulfonyl chlorides (V) and/or (VII) with a piperidine of formula VIII''' in the presence of a suitable base to scavenge the acid generated during the reaction. Suitable bases include, by way of examples, triethylamine, diisopropylethylamine, N-methylmorpholine and the like. The reaction is preferably conducted in solvents such as N,N-dimethylformamide, dimethylsulfoxide, N-methylpyrrolidone, ethanol, acetonitrile at a temperature from about 0° to about 100° C.

The specific sulfonamides of formula XIV—where $R^1$ is hydrogen—are readily prepared from the protected sulfonyl chlorides VII, by contacting said sulfonyl chlorides VII with an amine of formula VIII in the presence of a suitable base to scavenge the acid generated during the reaction. Suitable bases include, by way of examples, triethylamine, diisopropylethylamine, N-methylmorpholine and the like. The reaction is preferably conducted in solvents such as N,N-dimethylformamide, dimethylsulfoxide, N-methylpyrrolidone, ethanol, acetonitrile at a temperature from about 0° to about 100° C. The use of sulfonyl chloride of type VII leads to amines that have to be deprotected using well known methods by one skilled in the art to afford amine of general formula XIV

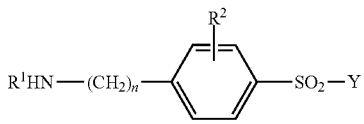

wherein $R^1$, $R^2$, Y and n are as above defined.

Derivatives of type XIV are then acylated according to described methods for the preparation of amides by condensation of amines with acid chlorides or carboxylic acids in the preferred conditions described above leading to compounds of general formula I A specific and preferred approach for preparing piperidino sulfonamides of formula I (Y is a piperidine VIII'''), wherein $L^1$ is a moiety —$NHR^3$, involves the following steps Reacting a cyanobenzene sulfonylchloride (XVa) with a protected piperidine-4-one;

Reduction of the nitrile (XVIa) to the amine (XVIIa);

Acylating the amine (XVIIa) to yield the benzamide (XVIIIa);

Deprotecting the piperidine-4-one moiety of the benzamide (XVIIIa);

Reacting the sulfonamide (XIX) having a reactive piperidine-4-one with a primary amine (reductive amination).

and is specified in Scheme 5:

$Ar^1$, $R^3$ and $R^2$ are as above defined.

For the preparation of piperidino sulfonamides of formula I, wherein n=0, a preferred method is set out in Scheme 6:

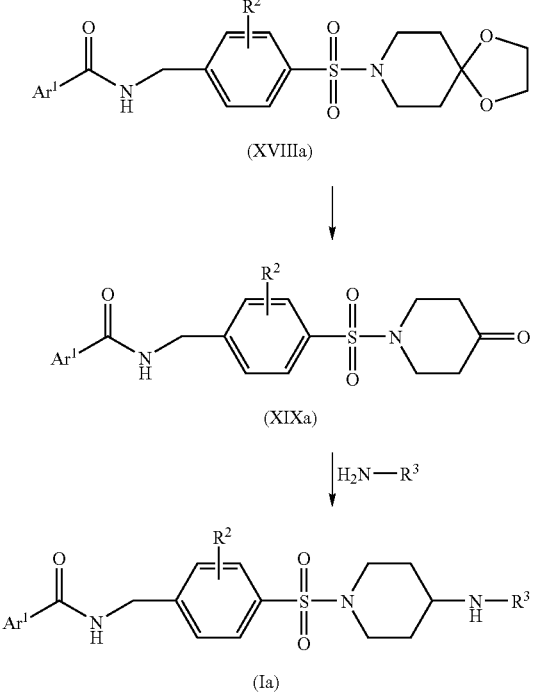

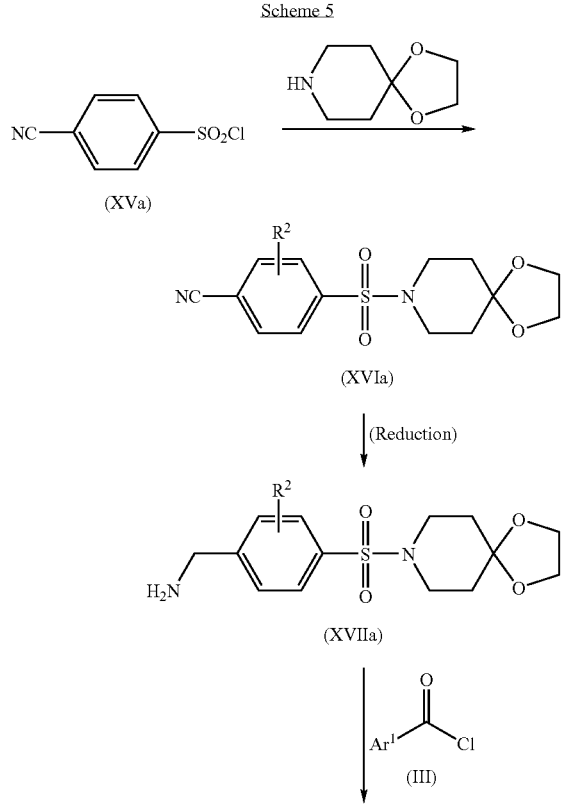

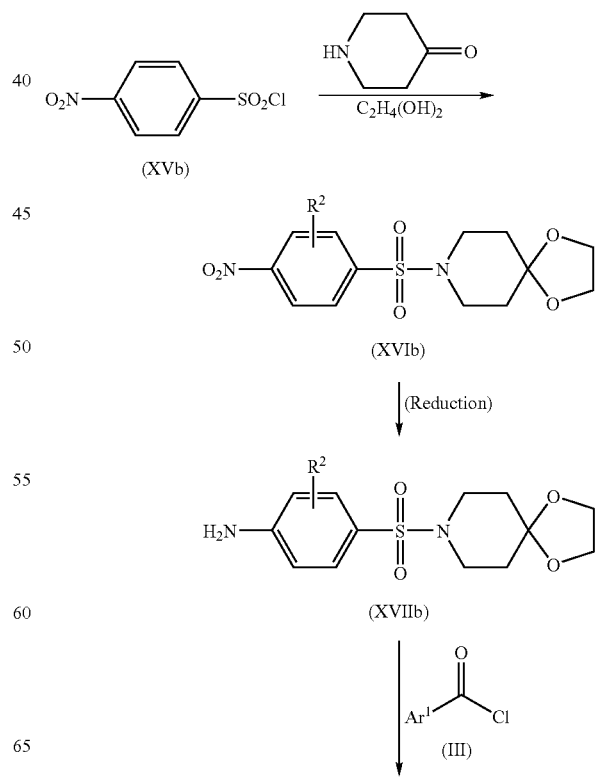

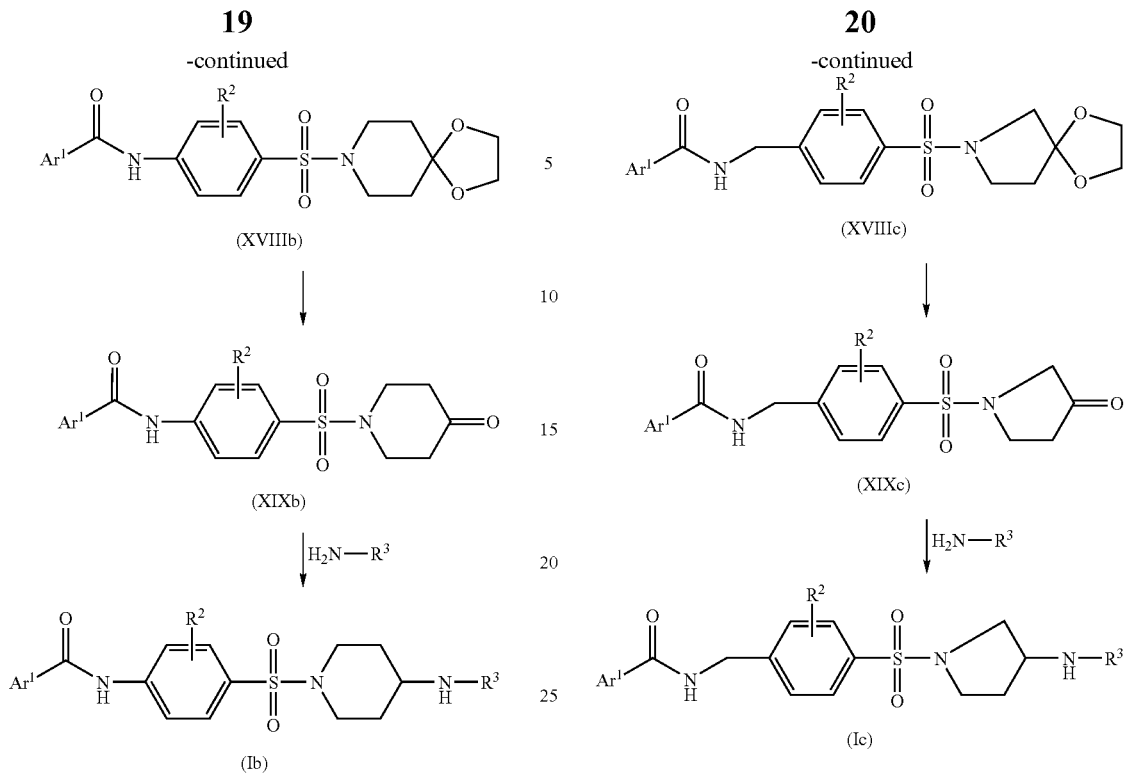

A specific and preferred approach for preparing pyrrolidino sulfonamides of formula I (Y is a pyrrolidine VIII"), wherein L¹ is a moiety —NHR³, is set out in Scheme 7:

Scheme 7

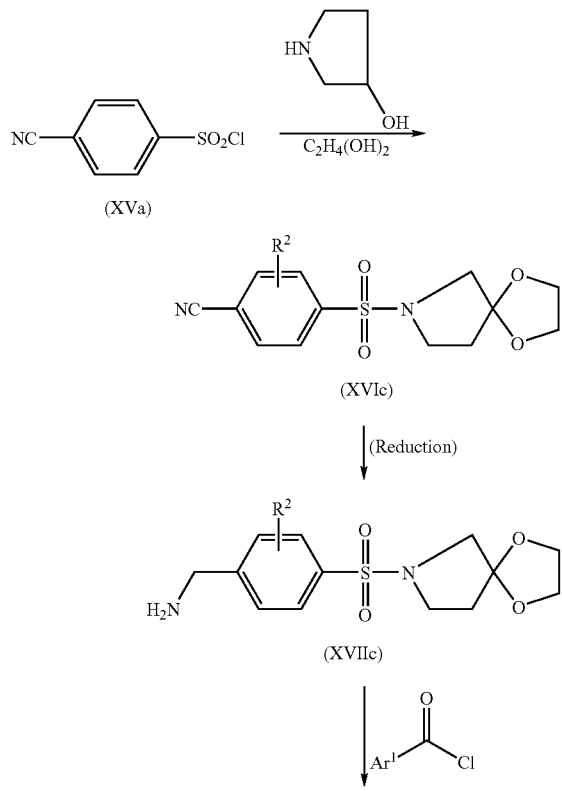

For the preparation of pyrrolidino sulfonamides of formula I, wherein n=0, the same pathways set out in Scheme 7 is performed, however by using the nitrobenzene sulfonyl chlorides instead of the cyanobenzene sulfonylchloride.

A specific approach for preparing sulfonamides of formula I where the central benzene group is substituted with hydrophilic groups (e.g. $R^2$ being a carboxylic group) involves the steps of providing the sulfonyl chloride (VII) wherein $R^1$ is a protecting group P;

reacting the sulfonyl chloride (VII) with an amine (VIII), e.g. a protected piperidin-4-one thus providing a sulfonamide (IX)

subjecting said sulfonamide (IX) to a metalation of $Ar^2$ to yield the corresponding substituted sulfonamide (IXa), removing protecting group P of said sulfonamide (IXa) and acylating the sulfonamide to yield compounds of formula (IXb)

deprotecting said sulfonamide (IXb) and to reductively aminate the corresponding ketone to yield compounds of formula I.

Said approach is specified in scheme 8:

Scheme 8:

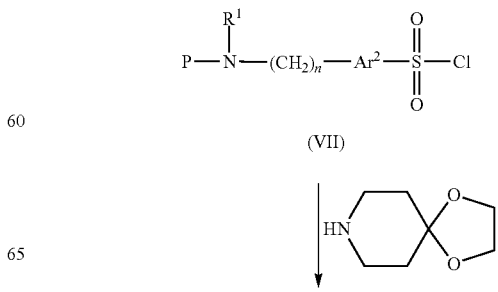

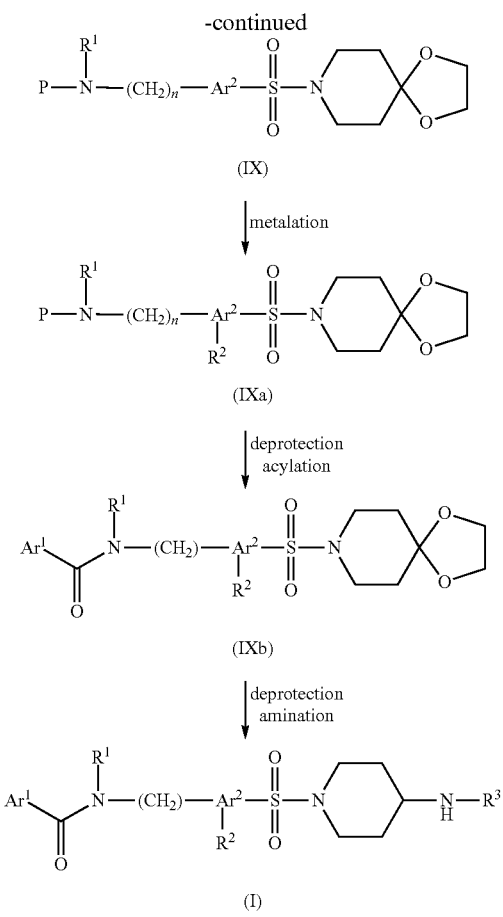

If the above set out general synthetic methods are not applicable for the obtention of compounds of formula I, suitable methods of preparation known by a person skilled in the art should be used. For example, one should start from commercially available 4-cyanobenzenesulfonyl chloride or 4-nitrobenzenesulfonylchloride and applies conventional methods known by a person skilled in the art to reach arylsulfonamide derivatives of formula I.

A further aspect of the present invention are sulfonamide compounds having the general formula (XIX) which are in particular useful for the preparation of the sulfonamide according to formula (I).

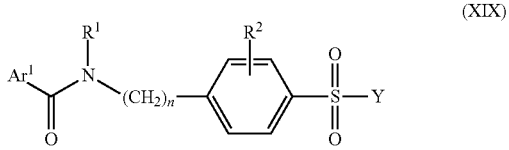

In said formula (XIX)
Ar$^1$ is an aryl or heteroaryl group;
R$^1$ is hydrogen or a C$_1$-C$_6$-alkyl group;
R$^2$ is hydrogen, —COOR$^3$, —CONR$^3$R$^3{}'$, OH, a C$_1$-C$_4$ alkyl substituted with an OH group, a hydrazido carbonyl group, a sulfate, a sulfonate, an amine or an ammonium salt;
n is either 0 or 1, and
Y is a pyrrolidine-3-one or a piperidine 4-one.

A final aspect of the present invention is related to the use of the compounds according to formula I for the modulation of the JNK function, or signaling pathways, the use of said compounds for the preparation of pharmaceutical compositions for the modulation of the JNK pathway as well as the formulations containing the active compounds according to formula I. Said modulation of the JNK pathway is viewed as a suitable approach of treatment for various disorders. When employed as pharmaceuticals, the benzsulfonamide derivatives of the present invention are typically administered in the form of a pharmaceutical composition. Hence, pharmaceutical compositions comprising a compound of formula I and a pharmaceutically acceptable carrier, diluent or excipient therefore are also within the scope of the present invention. A person skilled in the art is aware of a whole variety of such carrier, diluent or excipient compounds suitable to formulate a pharmaceutical composition. Also, the present invention provides compounds for use as a medicament. In particular, the invention provides the compounds of formula I for use as JNK inhibitor, notably JNK1 and/or JNK2 and/or 3, for the treatment of disorders of the immune as well as the neuronal system of mammals, notably of humans, either alone or in combination with other medicaments.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, the benzsulfonamides derivatives of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual com-pound administered, the age, weight, and response of the individual patient, the severity of the patient's symptoms, and the like.

The pharmaceutical compositions of these inventions can be administered by a variety of routes including oral, rectal, transdermal, subcutaneous, intravenous, intramuscular, and intranasal. Depending on the intended route of delivery, the compounds are preferably formulated as either injectable or oral compositions. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the benzsulfonamide compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or non-aqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring. Injectable compositions are typically based upon injectable sterile saline or phosphate-buffered saline or other injectable carriers known in the art. As above mentioned, the benzsulfonamide compound of formula I in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 8 of *Remington's Pharmaceutical Sciences, 17th Edition*, 1985, Marck Publishing Company, Easton, Pa., which is incorporated herein be reference. The compounds of this invention can also be administered in sustained release forms or from sustained release drug delivery systems. A description of representative sustained release materials can also be found in the incorporated materials in *Remington's Pharmaceutical Sciences*.

In the following the present invention shall be illustrated by means of some examples which are not construed to be viewed as limiting the scope of the invention.

EXAMPLES

Example 1

Protocol A

Preparation of 4-chloro-N-{4-[(4-{3-[(trifluoromethyl)sulfonyl]anilino}-1-piperidinyl)sulfonyl]benzyl}benzamide 1

4-[(4-{3-[(trifluoromethyl)sulfonyl]anilino}-1-piperidinyl)sulfonyl]benzonitrile 1a N-{3-[(trifluoromethyl)sulfonyl]phenyl}-4-piperidine (2.00 g, 6.49 mmol) was dissolved in THF (75 ml), 4-cyanobenzenesulfonyl chloride (1.57 g, 7.78 mmol) and Piperidine-PS (6.49 g, 9.73 mmol) were added and the mixture was shaken at room temp overnight. Excess sulfonyl chloride was scavenged with Aminomethyl-PS (5.9 g, 6.49 mmol) by shaking for further 4 h. The resins were filtered off, washed with THF (3×25 ml) and the combined filtrates evaporated to dryness yielding 2.8 g (91%) sulfonamide 4-[(4-{3-[(trifluoromethyl)sulfonyl]anilino}-1-piperidinyl)sulfonyl]benzonitrile 1a in >90% purity (LC-MS)

Preparation of Piperidine-PS:

Suspend Chloromethyl-PS (Merrifield) in 10 volumes of anhydrous DMF, add 2.5 equivalents of piperidine and stir at 65° C. for 18 h. Remove from heat and allow to rest at room temp for 4 h. Filter and wash resin with DMF, DCM, DMF, DCM, MeOH, DCM, MeOH, DCM and 3×THF. Dry resin in a vacuum oven for at least 4 h. IPC resin by conducting a chloranil test for the presence of free piperidine trapped in the resin (outcome should be negative—if positive, repeat washing cycle until chloranil test is negative). Capacity: 1.5 mmol/g.

1-{[4-(aminomethyl)phenyl]sulfonyl}-N-{3-[(trifluoromethyl)sulfonyl]phenyl}-4-piperidine 1b 4-[(4-{3-[(trifluoromethyl)sulfonyl]anilino}-1-piperidinyl)sulfonyl]benzonitrile (500 mg, 1.06 mmol) was dissolved in 1,4-dioxane (20 ml) and water (5 ml) and lithium hydroxide monohydrate (160 mg, 3.81 mmol) added. The reaction flask was evacuated and purged with nitrogen (3 times), 10% palladium on charcoal (100 mg, 0.094 mmol) and Raney-Nickel as 50% suspension in water (100 mg, 0.85 mmol) were added then the reaction flask was evacuated and purged with hydrogen (3 times). The mixture was shaken at room temperature under hydrogen atmosphere (balloon pressure) for 2 days, filtered through celite and washed with 1,4-dioxane/water (1:1, 40 ml). 1,4-dioxane was removed in vacuo, water (30 ml) was added to the residue and the obtained slurry extracted with ethyl acetate (3×25 ml). The combined organic layers were evaporated to dryness yielding amine 1-{[4-(aminomethyl)phenyl]sulfonyl}-N-{3-[(trifluoromethyl)sulfonyl]phenyl}-4-piperidine 1b as light yellow microcrystalline powder (400 mg, 79%) in >90% purity (LC-MS).

4-chloro-N-{4-[(4-{3-[(trifluoromethyl)sulfonyl]anilino}-1-piperidinyl)sulfonyl]-benzyl}benzamide 1

1-{[4-(aminomethyl)phenyl]sulfonyl}-N-{3-[(trifluoromethyl)sulfonyl]phenyl}-4-piperidine 1b (200 mg, 0.419) was dissolved in DCM (10 ml), Piperidine-PS (300 mg, 0.45 mmol) and 4-chlorobenzoyl chloride (75 mg, 0.42 mmol) as solution in DCM (5 ml) were added and the mixture was shaken at room temp overnight. Excess benzoyl chloride was scavenged with Aminomethyl-PS (50 mg, 0.06 mmol) by shaking for 2 h, DCM was removed in vacuo and the obtained residue purified by column chromatography on silica gel using a solvent gradient of 1-5% methanol in DCM. Fractions with $R_f$=0.13 (1% MeOH in DCM), $R_f$=0.62 (5% MeOH in DCM) were collected and evaporated to dryness. The residue was dissolved in DCM (5 ml) and 1 N HCl in ether (3 ml) was added. After aging at room temp for 1 h the precipitate was filtered off, washed with ether and dried in vacuo. The hydrochloride of the capped sulfonamide 4-chloro-N-{4-[(4-{3-[(trifluoromethyl)sulfonyl]anilino}-1-piperidinyl)sulfonyl]-benzyl}benzamide 1 was isolated as white powder (150 mg, 58%) in >95% purity, M/Z APCI 616.3 (M+1), 614.2 (M−1). $^1$H-NMR (DMSO-d$^6$) δ 9.36 (t, 1H, H—N5, $^3$J=5.92 Hz), 7.95 (d, 2H, $^3$J=8.65 Hz, H—C2,3), 7.75-7.64 (m, 4H, H—C7, 8, 9, 10), 7.59 (d, 2H, $^3$J=8.65 Hz, H—C1, 4), 7.49 (t, 1H, 8.20 Hz, H—C18), 7.20-7.10 (m, 3H, H—C17, 19, 20), 4.62 (d, 2H, $^3$J=5.92 Hz, H—C6), 3.57* (d, 2H, $^2$J=11.84 Hz, $H_{eq}$—C11, 15), 3.42 (m, br, 1H, H—C13), 2.57* (m, 2H under DMSO signal, $H_{ax}$—C12, 14), 1.95* (m, 2H, $H_{ax}$—C11, 15), 1.44* (m, 2H, $H_{eq}$—C12, 14), H—N16 exchanged.

The following table provides HPLC and mass spectrometry data of the mentioned examples.

| Example No | Compound Name | Rt HPLC | Purity (%) | Gradient HPLC | Mass M + 1 | Mass M − 1 |
|---|---|---|---|---|---|---|
| 2 | 4-chloro-N-{3-[(4-{3-[(trifluoromethyl)sulfonyl]anilino}-1-piperidinyl)sulfonyl]phenyl}benzamide | 5.6 | 99.0 | b | 602 | 600 |
| 3 | 4-chloro-N-{3-[(4-{3-[(trifluoromethyl)sulfonyl]anilino}-1-piperidinyl)sulfonyl]benzyl}benzamide | 5.4 | 97.0 | b | 616 | 614 |
| 4 | 4-chloro-N-{4-[(4-{3-[(trifluoromethyl)sulfonyl]anilino}-1-piperidinyl)sulfonyl]phenyl}benzamide | 5.6 | 95.0 | b | 602 | 600 |
| 5 | 2-hydroxy-N-{3-[(4-{3-[(trifluoromethyl)sulfonyl]anilino}-1-piperidinyl)sulfonyl]benzyl}nicotinamide | 4.3 | 99.0 | b | 599 | 597 |
| 6 | 2-hydroxy-N-{4-[(4-{3-[(trifluoromethyl)sulfonyl]anilino}-1-piperidinyl)sulfonyl]benzyl}nicotinamide | 4.3 | 100.0 | b | 599 | 597 |

Example 7

Protocol B; see Schemes 5 & 6

Preparation of 4-chloro-N-(4-{[4-(hexylamino)-1-piperidinyl]sulfonyl}benzyl)-benzamide (7)

Scheme for L1=ethylphenyl instead of n-hexyl 4-(1,4-dioxa-8-azaspiro[4.5]dec-8-ylsulfonyl)benzonitrile 7a 1,4-dioxa-8-azaspiro(4,5)decane (20.0 g, 0.14 mol), DCM (300 ml) and 1N aqueous sodium carbonate solution (200 ml) were charged to a flask and cooled to <10° C. A solution of 4-cyanobenzenesulfonyl chloride (26.8 g, 0.133 mol) in DCM (100 ml) was added dropwise, maintaining the temperature below 10° C. (typically addition takes 40-50 min). Cooling was removed and stirring at room temp continued for 2 h. The layers were separated, the organic layer was washed with water (2×100 ml) and concentrated in vacuo to approximately 100 ml. Hexane (about 300 ml) was added to initialise crystallisation. The precipitate was aged at 0-5° C. for 10-30 min, filtered and washed with hexane (2×100 ml) to yield 38.2 g (88%) of 4-(1,4-dioxa-8-azaspiro[4.5]dec-8-ylsulfonyl) benzonitrile 7a as white solid.

[4-(1,4-dioxa-8-azaspiro[4.5]dec-8-ylsulfonyl)phenyl]methanamine 7b

The catalyst (Aldrich Palladium, 5 wt % (dry basis) on activated carbon as 50 wt % suspension in water (Degussa type E101 NO/W), 3.0 g, 0.70=mol) was charged to a flask, which was evacuated and purged with nitrogen three times. A solution of nitrile 1a (14.0 g, 45.4 mmol) in ethanol (450 ml) and concentrated aqueous ammonium hydroxide solution (31 wt %, 40 ml, 620 mmol) were added. The flask was evacuated and purged with nitrogen three times then evacuated and filled with hydrogen twice. The reaction was stirred at room temp under hydrogen at balloon pressure and monitored by TLC (5% methanol in DCM) until complete (1-2 days). When complete, the flask was evacuated and purged with nitrogen three times, the catalyst was filtered off through a glass fibre filter paper and washed with hot ethanol (3×100 ml).

The reaction was worked up as follows: the filtrate was evaporated to dryness and the residue was purified by column chromatography on silica gel (25 fold weight of silica based on crude product) using a gradient elution with 5-50% methanol in DCM which yielded 90% of [4-(1,4-dioxa-8-azaspiro [4.5]dec-8-ylsulfonyl)phenyl]methanamine 7b.

In case where sulfonylphenyl benzamides are prepared, the starting compound 4 cyanobenzenesulfonyl chloride is replaced by the corresponding 4-nitrobenzenesulfonyl chloride leading to the corresponding aniline analogues (see scheme 6) the reaction time lasted 4-5 h. Work-up was carried out as follows: the filtrate was concentrated in vacuo to approximately 50 ml and cooled in an ice-acetone bath to initialise crystallisation (addition of water may be necessary in some cases). The precipitate was aged for 10-15 min, filtered and washed with ice-cold ethanol (2×30 ml). Yield=63-95%.

4-chloro-N-[4-(1,4-dioxa-8-azaspiro[4.5]dec-8-ylsulfonyl)benzyl]benzamide 7c

[4-(1,4-dioxa-8-azaspiro[4.5]dec-8-ylsulfonyl)phenyl] methanamine 7b (3.00 g, 10.1 mmol) was dissolved in DCM (20 ml), pyridine (976 µl, 12.1 mmol), 4-chlorobenzoyl chloride (1.41 ml, 11.1 mmol) and dimethylaminopyridine (catalytic amount) were added and the mixture was stirred at room temp overnight. Excess benzoylchloride was scavenged with aminomethyl-PS (2.0 g, 2.2 mmol) by shaking for 2 h. The resin was filtered off and washed with DCM (20 ml). The combined filtrates were washed with saturated aqueous citric acid (20 ml), dried over magnesium sulphate and evaporated to dryness to yield 2.7 g (59%) sulfonamide 4-chloro-N-[4-(1,4-dioxa-8-azaspiro[4.5]dec-8-ylsulfonyl)benzyl]benzamide 7c in >90% purity (LC-MS).

4-chloro-N-{4-[(4-oxo-1-piperidinyl)sulfonyl] benzyl}benzamide 7d 4-chloro-N-[4-(1,4-dioxa-8-azaspiro[4.5]dec-8-ylsulfonyl)benzyl]benzamide 7c (2.7 g, 5.99 mmol) was suspended in 6 N HCl (40 ml) and THF added until a clear solution was obtained (about 40 ml). The reaction mixture was stirred at room temp overnight and THF was removed in vacuo. The resulting suspension was diluted with cold water (50 ml), aged for 1 h at room temp and filtered. The filter residue was dried under high vacuum for several hours to yield 2.0 g (82%) of ketone 4-chloro-N-{4-[(4-oxo-1-piperidinyl)sulfonyl]benzyl}benzamide 7d as colourless powder in >90% purity (LC-MS).

4-chloro-N-(4-{[-4-(hexylamino)-1-piperidinyl] sulfonyl}benzyl)benzamide 7

4-chloro-N-{4-[(4-oxo-1-piperidinyl)sulfonyl] benzyl}benzamide 7d (500 mg, 1.23 mmol) was suspended in THF/methanol (10 ml/20 ml), N-hexylamine (149 mg, 1.48 mmol) and Cyanoborohydride-IRA400 (1.0 g, 3.0 mmol) were added and the reaction mixture was stirred at 50° C. overnight. Excess amine was scavenged with Ameba-PS (415 mg, 0.50 mmol) by shaking for 2 h. The resins were filtered off, solvent removed in vacuo and the obtained residue purified by column chromatography on silica gel using a step gradient of 2.5% methanol in DCM and 5% methanol in DCM. Fractions with $R_f$=0.28 (5% methanol in DCM,) were collected and evaporated to dryness (Note: Up to 1% conc. $NH_3$ (13.5 M) may be added during the chromatography to reduce loss of material). The residue was dissolved in DCM (10 ml) and 1 N HCl in ether (3 ml) added. After aging at room temp for 1 h the precipitate was filtered off and dried in vacuo. The hydrochloric salt of sulfonamide 4-chloro-N-(4-{[4-(hexylamino)-1-piperidinyl]sulfonyl}benzyl)benzamide 7 was isolated as off-white powder (260 mg, 36%) in >95% purity. M/Z APCI 492.0 (M+1), 490.2 (M−1). $^1$H-NMR (DMSO-d$^6$) (HCl salt) δ 9.39 (t, 1H, H—N5, $^3$J=5.92 Hz), 8.97 (m, br, 2H, H—N16), 7.99 (d, 2H, $^3$J=8.65 Hz, H—C2, 3), 7.75 (d, 2H, $^3$J=8.20 Hz, H—C8, 9), 7.61 (m, 4H, H—C1, 4, 7, 10), 4.61 (d, 2H, $^3$J=5.92 Hz, H—C6), 3.73* (d, 2H, $^2$J=11.84 Hz, H$_{eq}$—C11, 15), 3.07 (m, br, 1H, H—C13), 2.83 (m, br, 2H, H—C17), 2.29* (m, 2H, H$_{ax}$—C12, 14), 2.10* (d, br, 2H, $^2$J=11.90 Hz, H$_{ax}$—C11, 15), 1.71-1.54* (m, 4H, H$_{eq}$—C12, 14 and H—C18), 1.36-1.23 (m, 6H, H—C19, 20, 21), 0.89 (t, 3H, $^3$J=6.60 Hz, H—C22)

$^1$H-NMR (DMSO-d$^6$) (free base) δ 9.30 (t, 1H, H—N5, $^3$J=5.92 Hz), 7.97 (d, 2H, $^3$J=8.65 Hz, H—C2, 3), 7.73 (d, 2H, $^3$J=8.65 Hz, H—C8, 9), 7.61 (d, 2H, $^3$J=8.65 Hz, H—C1, 4), 7.59 (d, 2H, $^3$J=8.65 Hz, H—C7, 10), 4.69 (d, 2H, $^3$J=5.92 Hz, H—C6), 3.51* (d, 2H, $^2$J=11.84 Hz, H$_{eq}$—C11, 15), 2.55-2.40* (m, 5H, H—C13, 17, H$_{ax}$—C11, 15), 1.95-1.85* (m, 2H, H$_{ax}$—C12, 14), 1.46-1.26* (m, 10H, H$_{eq}$—C12, 14 and H—C18, 19, 20, 21), 0.94 (t, 3H, $^3$J=7.06 Hz, H—C22)

Preparation of Cyanoborohydride-IRA400:

100 ml of an aqueous solution of sodium cyanoborohydride (8% wt/vol—slightly turbid) is prepared and then passed through 10 g of wet, chloride form resin (Amberlite IRA400) on a sinter funnel. The resin is covered with one volume of cyanoborohydride solution, stirred and then the solution is removed under suction; the process is repeated ca. 10 times. The resulting resin is washed thoroughly with distilled water until free of excess sodium cyanoborohydride (to neutral pH), then dried by repeatedly washing with HPLC grade THF. The resulting average capacity should be 2.5-3.0 mmol/g of dry resin.

The below listed compounds (designated as Example No.) were prepared in a similar way by following the above set out protocol and using the corresponding starting compounds.

| Example No. | Compound Name | Rt HPLC | Purity (%) | Gradient HPLC | Mass M + 1 | Mass_M |
|---|---|---|---|---|---|---|
| 8 | 4-chloro-N-(3-{[4-(hexylamino)-1-piperidinyl]sulfonyl}phenyl)benzamide | 3.7 | 93.0 | b | 478 | 476 |
| 9 | 4-chloro-N-{4-[(4-{[4-(trifluoromethyl)benzyl]amino}-1-piperidinyl)sulfonyl]phenyl}benzamide | 3.8 | 98.0 | b | 552 | 550 |
| 10 | 4-chloro-N-(4-{[4-({2-[3-(trifluoromethyl)phenyl]ethyl}amino)-1-piperidinyl]sulfonyl}phenyl)benzamide | 4.0 | 98.0 | b | 566 | 564 |
| 11 | 4-chloro-N-(4-{[4-({2-[3-(trifluoromethyl)phenyl]ethyl}amino)-1-piperidinyl]sulfonyl}benzyl)benzamide | 3.83 | 99.0 | b | 580 | 578 |
| 12 | 4-chloro-N-(4-{[4-(hexylamino)-1-piperidinyl]sulfonyl}phenyl)benzamide | 3.8 | 99.5 | b | 478 | 476 |
| 13 | 4-chloro-N-(3-{[4-(hexylamino)-1-piperidinyl]sulfonyl}benzyl)benzamide | 3.6 | 99.9 | b | 492 | 490 |
| 14 | 4-chloro-N-{3-[(4-{[4-(trifluoromethyl)benzyl]amino}-1-piperidinyl)sulfonyl]benzyl}benzamide | 3.6 | 98.0 | b | 566 | 564 |
| 15 | 4-chloro-N-(3-{[4-({2-[3-(trifluoromethyl)phenyl]ethyl}amino)-1-piperidinyl]sulfonyl}benzyl)benzamide | 3.9 | 99.0 | b | 580 | 578 |
| 16 | 4-chloro-N-{4-[(4-{[4-(trifluoromethyl)benzyl]amino}-1-piperidinyl)sulfonyl]benzyl}benzamide | 3.6 | 99.8 | b | 566 | 564 |
| 17 | N-(4-{[4-(butylamino)-1-piperidinyl]sulfonyl}benzyl)-2-oxo-1,2-dihydro-3-pyridinecarboxamide | 1.9 | 99.0 | b | 446 | 444 |
| 18 | 4-chloro-N-{3-[(4-{[4-(trifluoromethyl)benzyl]amino}-1-piperidinyl)sulfonyl]phenyl}benzamide | 3.8 | 99.0 | b | 552 | 550 |
| 19 | N-{3-[(4-anilino-1-piperidinyl)sulfonyl]phenyl}-4-chlorobenzamide | 3.6 | 90.0 | b | 470 | 468 |
| 20 | 4-chloro-N-(3-{[4-({2-[3-(trifluoromethyl)phenyl]ethyl}amino)-1-piperidinyl]sulfonyl}phenyl)benzamide | 4.0 | 99.0 | b | 566 | 564 |
| 21 | N-(4-{[4-(hexylamino)-1-piperidinyl]sulfonyl}benzyl)-2-hydroxynicotinamide | 2.5 | 98.0 | b | 475 | 473 |
| 22 | N-(3-{[4-(hexylamino)-1-piperidinyl]sulfonyl}benzyl)-2-hydroxynicotinamide | 2.6 | 97.0 | b | 475 | 473 |

Example 23

Protocol C; see Scheme 7

Preparation of 4-chloro-N-(4-{[3-({2-[3-(trifluoromethyl)phenyl]ethyl}amino)-1-pyrrolidinyl]sulfonyl}benzyl)benzamide 23

4-[(3 hydroxy-1-pyrrolidinyl)sulfonyl]benzonitrile 23a 4-hydroxypyrrolidine (12 g, 0.14 mol), DCM (300 ml) and 1N aqueous sodium carbonate solution (200 ml) were charged to a flask and cooled to <10° C. A solution of 4-cyanobenzenesulfonyl chloride (26.8 g, 0.133 mol) in DCM (100 ml) was added drop-wise, maintaining the temperature below 10° C. (typically addition takes 40-50 min). Cooling was removed and stirring at room temperature continued for 2 h. The layers were separated, the organic layer was washed with water (2×100 ml) and concentrated in vacuo to approximately 100 ml. Hexane (about 300 ml) was added to initialise crystallisation. The precipitate was aged at 0-5° C. for 10-30 min, filtered and washed with hexane (2×100 ml) to yield 30.3 g (86%) of sulfonamide 4-[(3-hydroxy-1-pyrrolidinyl)sulfonyl]benzonitrile 23a as white solid.

4-[(3-oxo-1 pyrrolidinyl)sulfonyl]benzonitrile 23b

4-[(3-hydroxy-1-pyrrolidinyl)sulfonyl]benzonitrile 23a (17.0 g, 67.3 mmol) was dissolved in DCM (300 ml) and treated at room temp with PS-TEMPO (capacity: 1.17 mmol/g, 400 mg, 0.74 mmol). Then 5% aqueous sodium hydrogencarbonate solution (150 ml) was added and the mixture stirred vigorously while cooling to 10° C. Aqueous sodium hypochlorite (titrated at 7.0 wt % NaOCl*; 77.6 ml, 93.0 g, 87.5 mmol) was added over 40 min, maintaining the temperature below 10° C. Cooling was removed and the reaction mixture stirred vigorously. TLC after 2 h showed no starting material, therefore the stirring was stopped and layers separated. The aqueous layer was extracted with DCM (2×30 ml), and the combined organic layers washed with saturated aqueous sodium thiosulphate (75 ml) then water (150 ml). Each of these aqueous layers were back-extracted with DCM (30 ml) and combined with the main organic extract, which was then filtered through a cotton wool plug and evaporated to dryness, yielding 14.3 g (85%) ketone 4-[(3-oxo-1-pyrrolidinyl)sulfonyl]benzonitrile 23b.

4-(1,4-dioxa-7-azaspiro[4.4]non-7-ylsulfonyl)benzonitrile 23c

4-[(3-oxo-1-pyrrolidinyl)sulfonyl]benzonitrile 23b (11.6 g, 46.3 mmol) was suspended in toluene (110 ml) and stirred at room temp. Ethylene glycol (6.2 ml, 6.9 g, 111 mmol) and para-toluene sulphonic acid monohydrate (100 mg, 0.53 mmol) were added. The reaction mixture was heated to reflux under Dean-Stark conditions and monitored by water collection and TLC (5% methanol in DCM). If necessary for the completion of the reaction (typically within 3 h), further portions of p-TSA were added. When complete the reaction mixture was washed with saturated sodium bicarbonate solution (55 ml) and water (2×55 ml). The organic layer was filtered through cotton wool and then concentrated in vacuo to approximately 50 ml or until precipitation started. Hexane (150 ml) was added and the suspension stirred at 0-5° C. for 10-20 min, filtered and washed with hexane (2×50 ml). The residue was air dried to yield 13.0 g (96%) ketal 4-(1,4-dioxa-7-azaspiro[4.4]non-7-ylsulfonyl)benzonitrile 23c. 4-(1,4-dioxa-7-azaspiro[4.4]non-7-ylsulfonyl)benzonitrile 23c was progressed according to the procedure described for example 7b which finally leads to 4-chloro-N-(4-{[3-({2-[3-(trifluoromethyl)phenyl]ethyl}amino)-1-pyrrolidinyl]sulfonyl}benzyl)benzamide 23. M/Z APCI 566.0 (M+1), 564.2 (M−1), $^1$H-NMR (DMSO-d$^6$) δ9.57 (m, 2H, H—N15), 9.42 (t, 1H, H—N5, $^3$J=5.92 Hz), 7.99 (d, 2H, $^3$J=8.65 Hz, H—C2, 3), 7.82 (d, 2H, H—C8, 9), 7.71-7.59 (m, 8H, H—C1,4,7,10,18,19,20,21), 4.62 (d, 2H, $^3$J=5.92 Hz, H—C6), 3.75 (m, 1H, H—C12), 3.53-3.33 (m, 2H under DMSO-H$_2$O signal, H—C16), 3.27-3.03 (m, 6H, H—C11, 14, 17), 2.17 (m, 1H, H$_a$—C13), 2.04 (m, 1H, H$_b$—C13).

after D$_2$O-exchange:

$^1$H-NMR (DMSO-d$^6$) δ 7.99 (d, 2H, $^3$J=8.65 Hz, H—C2, 3), 7.82 (d, 2H, H—C8, 9), 7.71-7.59 (m, 8H, H—C1,4,7,10,18,19,20,21), 4.58 (s, 2H, H—C6), 3.74 (m, 1H, H—C12), 3.47-3.33 (m, 2H, H—C16), 3.32-3.23 (m, 1H, H$_a$—C14), 3.22-3.14 (m, 2H, H—C11), 3.13-3.04 (m, 1H, H$_b$—C14), 3.03-2.94 (m, 2H, H—C17), H—C11, 14, 17), 2.17 (m, 1H, H$_a$—C13), 1.94 (m, 1H, H$_b$—C13)

The below listed compounds (designated as Example No.) were prepared in a similar way by following the above set out protocol and using the corresponding starting compounds.

| Example No. | Compound Name | Rt HPLC | Purity (%) | Gradient HPLC | Mass M + 1 | Mass_M |
|---|---|---|---|---|---|---|
| 24 | 4-chloro-N-(3-{[3-(hexylamino)-1-pyrrolidinyl]sulfonyl}-phenyl)benzamide | 3.6 | 99 | b | 464 | 462 |
| 25 | 4-chloro-N-(3-{[3-({2-[3-(trifluoromethyl)phenyl]ethyl}amino)-1-pyrrolidinyl]sulfonyl}-phenyl)benzamide | 4 | 98 | b | 552 | 550 |
| 26 | 4-chloro-N-{4-[(3-{[4-(trifluoromethyl)benzyl]amino}-1-pyrrolidinyl)sulfonyl]-phenyl}benzamide | 3.7 | 98 | b | 538 | 536 |
| 27 | 4-chloro-N-{4-[(3-{[2-[3-(trifluoromethyl)phenyl]ethyl}amino)}-1-pyrrolidinyl)sulfonyl]-phenyl}benzamide | 4 | 96 | b | 552 | 550 |
| 28 | 4-chloro-N-(4-{[3-(hexylamino)-1-pyrrolidinyl]sulfonyl}-phenyl)benzamide | 3.7 | 91 | b | 464 | 462 |

-continued

| Example No. | Compound Name | Rt HPLC | Purity (%) | Gradient HPLC | Mass M + 1 | Mass_M |
|---|---|---|---|---|---|---|
| 29 | 4-chloro-N-(4-{[3-({2-[3-(trifluoro-(trifluoromethyl)-phenyl]ethyl}amino)-1-pyrrolidinyl]sulfonyl}-phenyl)benzamide | 3.6 | 98 | b | 552 | 550 |
| 30 | 4-chloro-N-{3-[(3-{[4-(trifluoromethyl)benzyl]amino}-1-pyrrolidinyl)-sulfonyl]-benzyl}benzamide | 3.7 | 99 | b | 552 | 550 |
| 31 | 4-chloro-N-(4-{[3-({2-[3-(trifluoromethyl)phenyl]ethyl}amino)-1-pyrrolidinyl]sulfonyl}-benzyl)benzamide | 3.8 | 98 | b | 566 | 564 |

Example 32

Preparation of a Pharmaceutical Formulation

The following formulation examples illustrate representative pharmaceutical compositions according to the present invention being not restricted thereto.
Formulation 1—Tablets
An benzsulfonamide compound of formula I is admixed as a dry powder with a dry gelatin binder in an approximate 1:2 weight ration. A minor amount of magnesium stearate is added as a lubricant. The mixture is formed into 240-270 mg tablets (80-90 mg of active benzsulfonamide compound per tablet) in a tablet press.
Formulation 2—Capsules
An benzsulfonamide compound of formula I is admixed as a dry powder with a starch diluent in an approximate 1:1 weight ratio. The mixture is filled into 250 mg capsules (125 mg of active benzsulfonamide compound per capsule).
Formulation 3—Liquid
A benzsulfonamide compound of formula I (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.
Formulation 4—Tablets
A benzsulfonamide compound of formula I is admixed as a dry powder with a dry gelatin binder in an approximate 1:2 weight ratio. A minor amount of magnesium stearate is added as a lubricant. The mixture is formed into 450-900 mg tablets (150-300 mg of active furansulfonic acid compound) in a tablet press.
Formulation 5—Injection
A benzsulfonamide compound of formula I is dissolved in a buffered sterile saline injectable aqueous medium to a concentration of approximately 5 mg/ml.

Example 33

Biological Assays

Biological Results
The biological activities of the compounds according to formula I may be assessed using the following in vitro and in vivo assays.

JNK2 and -3 In Vitro Assays:
The phosphorylation of c-jun by JNK2 or JNK3 may be followed by monitoring the incorporation of $^{33}P$ into c-jun following the protocol below. The inhibitory activity of the compounds according to formula I in respect of c-jun phosphorylation through JNK, is determined by calculating the phosphorylation activity of a JNK in the presence or absence of the test compounds according to formula I.

JNK3 and/or -2 assays are performed in 96 well MTT plates: incubation of 0.5 µg of recombinant, pre-activated GST-JNK3 or GST-JNK2 with 1 µg of recombinant, biotinylated GST-c-Jun and 2 µM $^{33}\gamma$-ATP (2 nCi/µl), in the presence or absence of compounds according to formula I and in a reaction volume of 50 µl containing 50 mM Tris-HCl, pH 8.0; 10 mM $MgCl_2$; 1 mM Dithiothreitol, and 100 µM $NaVO_4$. The incubation is performed for 120 min. at R.T and stopped upon addition of 200 µl of a solution containing 250 µg of Streptavidine-coated SPA beads (Amersham, Inc.)*, 5 mM EDTA, 0.1% Triton X-100 and 50 µM ATP, in phosphate saline buffer.

After incubation for 60 minutes at RT, beads are sedimented by centrifugation at 1500×g for 5 minutes, resuspended in 200 µl of PBS containing 5 mM EDTA, 0.1% Triton X-100 and 50 µM ATP and the radioactivity measured in a scintillation β counter, following sedimentation of the beads as described above. By replacing biotinylated GST-c Jun with biotinylated $GST-_1ATF_2$ or biotinylated myelin basic protein, this assay may also be used to measure inhibition of pre-activated p38 and ERK MAP Kinases, respectively.

| Example No | JNK3 $IC_{50}$ (µM) | JNK2 $IC_{50}$ (µM) |
|---|---|---|
| 11 | <0.4 | <0.7 |
| 28 | <0.4 | <0.7 |
| 3 | <0.4 | <0.7 |
| 31 | <0.4 | <0.7 |

The values indicated in respect of JNK2 and 3 refer to the $IC_{50}$ (µM), i.e. the amount necessary to achieve 50% inhibition either of JNK3 or JNK2.

The tested compounds according to formula I display an inhibition ($IC_{50}$) with regard to JNK3 of less than 0.4 µM, more preferred of equal or less than 0.2 µM.

The tested compounds according to formula I display an inhibition ($IC_{50}$) with regard to JNK2 of less than 0.2 µM, more preferred equal or less than 0.02 µM.

Sympathetic Neuron Culture and Survival Assay

The ability of the compounds according to formula I to increase the survival rate of neuronal cells having been induced to cell death was assessed using the following protocol Sympathetic neurons from superior cervical ganglia (SCG) of new-born rats (p4) are dissociated in dispase, plated at a density of $10^4$ cells/cm$^2$ in 48 well MTT plates coated with rat tail collagen, and cultured in Leibowitz medium containing 5% rat serum, 0.75 μg/mL NGF 7S (Boehringer Mannheim Corp., Indianapolis, Ind.) and arabinosine $10^5$M. Cell death is induced at day 4 after plating by exposing the culture to medium containing 10 μg/mL of anti NGF anti-body (Boehringer Mannheim Corp., Indianapolis, Ind.) and no NGF or arabinosine, in the presence or absence of sulfonamide inhibitors. 24 hours after cell death induction, determination of cell viability is performed by incubation of the culture for 1 hour, at 37° C. in 0.5 mg/mL of 3-(4,5-dimethylthiazol-2-yl)2,5 diphenyl tetrazolium bromide (MTT). After incubation in MTT cells are resuspended in DMSO, transferred to a 96 MTT plate and cell viability is evaluated by measuring optical density at 590 nm.

The results of this assay with various test compounds demonstrate that compounds of Formula I are rescuing neurons from cell death (% neurons alive between 10 and 80).

IL-2 Release Assay:

The ability of the compounds according to formula I to modulate the inflammatory response by inhibiting the release of IL-2 was assessed using the following protocol JNK pathway activation triggers the production of inflammatory cytokines such as IL-2. JNK can be activated by external stimuli such as PMA and Ionomycine and IL-2 production can be measured via an IL-2 ELISA test. Comparative measurements with and without the compounds of the invention according to the following protocol measure the ability of the compounds to prevent to stress-mediated IL-2 release.

Jurkat cells, a human T cell leukemia cell line (American Type Culture Collection # TIB 152) were cultured in RPMI 1640 medium (Gibco; BRL) supplemented with 10% of heat-activated fetal calf serum (FCS), Glutamine and Penstrep. The cell suspension in the medium is diluted to give $2.10^6$ cells/mL. The cells were plated ($2.10^5$ cells/well) on a 96-well plate containing different concentrations of a compound according to formula I (final concentration of compounds, 10, 3, 1, 0.3, 0.1 μM). This mixture is incubated 30 minutes at 37° C. in a humidified CO$_2$ atmosphere. Cells were then treated with 10 μl PMA (Phorbolmyristate-13 Acetate-12)+Ionomycine (0.1 μM and 1 μM final concentration) in all wells except negative control. In wells without compounds, 10 μl of RPMI 2% DMSO (=0.1% final) is added. Cells are incubated 24 hours at 37° C. and then the supernatant harvested (freeze at −20° C. if not used the same day) prior to performing IL-2 ELISA test on the supernatant.

IL-2 ELISA Assay:

IL-2 release into the medium by (PMA+Iononomycin)-stimulated Jurkat cells, in presence or absence of test compounds may be assayed by ELISA. Following the procedure described below.

Monoclonal anti-human IL-2 antibody (MAB602) (capture), biotinylated anti-human IL-2 antibody (BAF202) (detection) and recombinant human IL-2 (202-IL-010) (standard) from From R&D Systems are used.

Plate Preparation

100 μl capture antibody diluted in PBS at 5 μg/mL (PBS—Tween 0.05%) are transferred into a 96 well ELISA plate and incubated overnight at room temperature.

Each well is aspirated and washed 3 times with wash buffer (PBS—Tween 0.05%). After the last wash, the plate is damped.

Assay Procedure 1. 100 μl of sample or standard are added (2000, 1000, 500, 250, 125, 62.5, 31.25 pg/mL) and incubated 2 hours at room temperature.
2. 3-time-wash
3. 100 μl of biotinylated anti-human IL-2 at 12.5 ng/mL are added and incubated 2 hours at room temperature.
4. 3-time-wash
5. 100 μl streptavidin-HRP (Zymed #434323) at 1:10,000 are added and incubate 30 minutes at room temperature.
6. 3-time-wash
7. 100 μl substrate solution (citric acid/Na$_2$HPO$_4$ (1:1)+H$_2$O$_2$ 1:2000+OPD) are added and incubated 20-30 minutes at room temperature.
8. 50 μl of stop solution (H$_2$SO$_4$ 20%) are added to each well.
9. Optical density is measured using a microtiter plate reader set to 450 nm with correction at 570 n.

The result of this assay shows that various test compounds decrease the production of IL-2 of more than 30% at 3 μM.

C-Jun Reporter Assay

The phosphorylation of the transcriptional factor, c-jun, by JNK in the MAP kinase signal transduction pathway may be followed via a trans-reporting system such as the commercially available PathDetect® (32).

Inhibition of phosphorylation by using compounds according to formula I can then be assessed.

A trans-reporting system allows one to follow, via Luciferase activity, the activation status of a fusion trans-activator protein. The trans-activator protein consists of the activation domain of the transcriptional factor of interest (c-jun) fused with a yeast transcriptional activator, GAL4 DNA binding domain (dbd). The GAL4 dbd has the advantage that no known mammalian transcriptional factors can bind to it and therefore the background noise of the assay is very low.

In the present case, Hela luciferase reporter-c-Jun (HLR-c-Jun) cell lines which constitutively express GAL4-cJun were used.

The MEKK-1 gene was inserted. MEKK-1 is a MAPKKK which triggers the activation of JNK. Expression of wild type MEKK-1 is sufficient for JNK activation (33). Once, JNK is activated it can induce the phosphorylation of the c-jun domain of the fusion trans-activator protein (GAL4 dbd-cjun) which forms a dimer. The dimer is then is able to bind to a GAL4 upstream activating sequence (GAL4 UAS) of the reporter which activates Luciferase expression.

Luciferase expression is detected by luminescence using a simple assay such as Dual-Luciferase® Reporter Assay System (34) in which *Renilla* is used as a "control reporter".

Inhibition of JNK is observed as a decrease in Luciferase expression and detected by a decrease in luminescence.

Cell Culture

HLR-c-Jun cells are cultured in DMEM High Glc supplemented with 10% FCS (Sigma), 2 mM Glutamine (Gibco), P/S, Hygromycin b 100 μg/mL and G418 250 μg/mL.

Cell Culture Preparation

Cell Banks

The cells are stored frozen in cryotubes under liquid nitrogen, as 1.8 mL volumes of cell suspension in culture medium containing 10% dimethyl sulfoxide.

Cell Culture Thawing

When necessary, frozen vials of cells are thawed rapidly at 37° C. in a water bath by gently swirling up to semi-complete thawing. Then the cell suspension is added to 10 mL of culture medium and then centrifuged for 5 minutes at 1200 rpm. The supernatant is removed and the cell pellet reconstituted in the medium. The flasks are incubated at 37° C. in an atmosphere of 5% $CO_2$.

Cell Passage

The cells are serially sub-cultured (passaged) when 80% confluent monolayers have been obtained.

The medium of each flask is removed and the monolayer is washed with 10-15 mL of phosphate buffer solution (PBS).

Trypsin-EDTA solution is added to the cell monolayer, incubated at 37° C. and tapped gently at intervals to dislodge the cells. Complete detachment and disaggregation of the cell monolayer is confirmed by microscopy examination. The cells are then re-suspended in 10 mL of complete medium and centrifuged for 5 minutes at 1200 rpm. The supernatants are discarded, the cells are re-suspended in culture medium and diluted ⅕ in 175 $cm^2$ flasks.

Day 0 Morning

Prepare Cells for Transfections

The cells of near-confluent cultures are detached and disaggregated by treatment with trypsin as described above.

The cells are re-suspended in culture medium and counted.

The cell suspensions are diluted with medium to give about $3.5 \times 10^6$ cells/mL and 1 mL µl of cell suspension are put onto 2 10 cm culture dishes containing 9 mL of culture medium.

The plates are incubated at 37° C. in a humidified atmosphere of 5% $CO_2$ in air.

Day 0 Evening

Transfections

Control: 0.2 µg pTK *Renilla*, 5.8 µg pBluescript KS, 500 µl OPTIMEM (GIBCO), 18 µl Fugene 6.

Induced: 0.1 µg pMEKK1, 0.2 µg pTK *Renilla*, 5.7 µg pBluescript KS, 500 µl OPTIMEM (GIBCO), 18 µl Fugene 6 30' RT.

The transfection mixture is added to the plated cells. The plates are incubated over night at 37° C. in a humidified atmosphere of 5% $CO_2$ in air.

Day 1

A 96 wells plate (100 µl of culture medium per well) is prepared.

Negative control (vehicle): 2 µl of DMSO is added to the 100 µl (in triplicate).

2 µl of compound according to formula I stock dilutions (3, 1 and 0.1mM in 100% DMSO) are added to the 100 µl (in triplicate).

The transfected cells are trypsinised and re-suspended in 12 mL of culture medium.

100 µl of the dilution are added to each of the 96 wells plate.

The plate is incubated over night at 37° C. in a humidified atmosphere of 5% $CO_2$ in air.

Day 2

Test procedure: Dual-Luciferase® Reporter Assay System (34).

The medium is removed from the plate and the cells are washed two times with 100 µl PBS. Lysis reagent is applied (Passive Lysis Buffer, PLB). Into each culture well 5 µl of 1×PLB are dispensed. The culture plates are placed on a rocking platform or orbital shaker with gentle rocking/shaking to ensure complete coverage of the cell monolayer with 1×PLB. The culture plates are rocked at room temperature for 15 minutes. 20 µl of the lysate are transferred into a white opaque 96 well plate. The luminometer reading is recorded.

−50 µl of Luciferase Assay Reagent II are injected and readings are recorded at 5 and 10 minutes.

50 µl of Stop & Glo® Reagent are injected and readings are recorded at 5 and 10 minutes.

The relative luminescence is then measured: RLU Luciferase/RLU *Renilla*.

The result of this assay shows that various test compounds inhibit more than 20% of the activity of JNK at 10 µM.

LPS Induced Endotoxin Shock in Mice

The ability of the JNK inhibitors described in formula I to significantly reduce the level of inflammatory cytokines induced by LPS challenge was assessed using the following protocol:

Endotoxins are the lipopolysaccharides (LPS) constituents of the outer membrane of Gram negative bacteria. Response to LPS has been shown to involve the activation of different cell populations and to lead to the expression of various inflammatory cytokines that include tumor necrosis factor-alpha (TNFα) and interferon gamma (IFN-γ). As LPS is known to stimulate the activation of various MAP kinase pathways, including JNK (35), the ability of JNK inhibitors can be tested after the JNK signaling pathway has been switched on by a LPS challenge.

The activity as JNK inhibitors of compounds of formula may be assessed after a LPS challenge using the following protocol:

LPS (*S. abortus*-Galanos Lab.-) is injected (200 µg/kg, i.v.) to Male C57BL/6 mice to induce endotoxin shock. Compounds according to formula I (0.1, 1, 10 mg/kg) or NaCl (200 uM) are injected intravenously (10 mL/kg) 15 min before the LPS challenge. Heparinized blood was obtained from the orbital sinus at different time points after the LPS challenge, and the blood was centrifuged at 9,000 rpm for 10 min at 4° C. to collect supernatant. Measurement of cytokines production such as TNFα and IFNγ by mouse is performed with an ELISA kit such as Duoset® DY410 for TNFα and DY 485 for IFN γ. Other ELISA assays such as described in (36) can be used.

Global Ischemia in Gerbils

The ability of the JNK inhibitors described in formula I to protect cell death during a stroke event was assessed using the following protocol:

The gerbil bilateral carotid occlusion is a well-described animal model of acute ischemic stroke and involves relatively easy surgical techniques.

The neuronal degeneration in the hippocampus develops over several days and is often referred as "delayed neuronal death". In addition, the neurodegeneration observed histologically is obvious and easily quantified (37). Furthermore, the histopathology seen in the gerbil is similar to that observed in the hippocampal CA1 region of the human brain following a cardiac arrest. Behavior observations, such as memory tests, could even be performed in the case of gerbils. This kind of tests for appreciation of the degree of recovery is not easily manageable in other models such as in rat whose learning abilities are much poorer (38).

The neuroprotective effect according to formula I to protect may be assessed using the gerbil global ischemia model and such a protocol:

—1—METHOD

Surgery

Anesthesia with isoflurane (0.5-4%).

The common carotid arteries (left and right) are freed from tissue.

Occlusion of the arteries using Bulldog microclamps during 5 min.

Removal of clamps (reperfusion)

Stabulation of the animals under heating lamp until awake.

Stabulation of the animals in the animalry in individual cages.

Sacrifice of the animals
  7 days after ischemia (Decapitation or overdose of pentobarbital).
  Sampling of the brain.
Histological parameters
  Freezing of the brain in isopentane (−20° C.)
  Slicing of the hippocampus using a cryo-microtome (20 μm).
  Staining with cresyl violet method
  Evaluation of the lesions (in CA1/CA2 subfields of the hippocampus) by a modified Gerhard & Boast score (39).
—2—TREATMENT
  Administration of the compound according to formula I or the vehicle: 15 min, 24 hours and 48 hours after reperfusion (5-10 min after the recovery of the anesthesia).
  Standard protocol
  50 animals: 5 groups of 8 (group A: control, groups B-D: test article at 3 doses and group E: reference compound (Orotic acid 3×300 mg/kg, ip).

The test compounds displayed considerable capability to protect from neuronal apoptosis during induced global ischemia.

REFERENCES

1. Davis, Roger J., Signal Transduction by the JNK Group of MAP Kinases. *Cell*, 2000, 103: 239-252.
2. Chen, Yi-Rong and Tan, Tse-Hua. The c-Jun N-terminal kinase pathway and apoptotic signaling. *International Journal of Oncology*, 2000, 16: 651-662
3. Ip, Y T. and Davis R J, Signal transduction by the c-Jun N-terminal kinase (JNK) from c-Jun N-terminal kinase (JNK) from inflammation to development *Curr Opin Cell Biol* 1998, 10:205-219.
4. Leppä, S. and Bohmann D., Diverse functions of JNK signalling and c-Jun in stress response and apoptosis, *Oncogene* 1999, 18(45):6158-6162.
5. Minden, A. and Karin M. Regulation and function if the JNK subgroup of MAP kinases. *Biochim Biophys Acta* 1997, 1333:F85-F104.
6. Whitmarsh, A. J., and Davis. R. J. Transcription factor AP-1: regulation by mitogen activated protein kinases signal transduction pathways. *J. Mol, Med.* 1996, 77, 2360-2371.
7. Gupta, S. et al., Selective interaction of JNK protein kinase isoforms with transcription factors. *The EMBO Journal*, 1996, 158(11): 2760-2770.
8. Derek D. et al., Absence of excitotoxicity-induced apoptosis in the hippocampus of mice lacking the Jnk3 gene. *Nature* 1997, 389:865-876.
9. Martin, Loel H. et al., Developmental expression in the mouse nervous system of the p49$^{3F12}$ SAP kinase. *Molecular Brain Research*, 1996, 35: 47-57.
10. Kumagae, Y. et al., Human c-Jun N-terminal kinase expression and activation in the nervous system, *Molecular Brain Research* 1999, 67: 10-17
11. Dumitru, Calin D. et al. TNF-alpha induction by LPS is regulated posttranscriptionally via a Tpl2/ERK-dependent pathway. *Cell* 2000, 103: 1071-1083.
12. Han, Z. et al., C-Jun N-terminal kinase is required for metalloproteinase expression and joint destruction in inflammatory arthritis. *The Journal of Clinical Investigation* 2001, 108 (1):73-81.
13. Nishina, H., et al. Impaired CD28-mediated interleukin 2 production and proliferation in stress kinase SAPK/ERK1 kinase (SEK1)/mitogen-activated protein kinase kinase 4 (MKK4)-deficient T lymphocytes. *Journal of Experimental Medicine* 1997, 186(6): 941-953.
14. Kempiak, Stephan J. et al. The Jun Kinase Cascade is responsible for activating the CD28 Response element of the IL-2 Promoter: proof of cross-talk with the IKB Kinase Cascade, *The Journal of Immunology*, 1999, 162: 3176-3187.
15. De la Monte, S. M. et al., Oxygen free radical injury is sufficient to cause some Alzheimer-type molecular abnormalities in human CNS neuronal cells. *J. Alzheimer's Dis.* 2000, 2(3-4): 261-281.
16. Zhu, X, Activation and redistribution of c-Jun N-terminal kinase/stress activated protein kinase in degenerating neurons in Alzheimer's disease. *Journal of Neurochemistry* 2001, 76: 435-441
17. Force, T. et al., Stress-Activated Protein Kinases in cardiovascular Disease. *Circulation Research*. 1996, 78:947-953.
18. Kim, S. et al., Angiotensin blockade inhibits activation of mitogen-activated Protein Kinases in Rat balloon-injured artery. Circulation 1998, 97:1731-1737.
19. Xu, Q. et al., Acute Hypertension Activates Mitogen-activated Protein Kinases in Arterial Wall. *The Journal of Clinical Investigation* 1996, 97 (2):508-514.
20. Bogoyevitch, M. A. et al., Stimulation of the stress-activated mitogen-activated protein kinase subfamilies in perfused heart. *Circulation Research*. 1996, 79:162-173.
21. Pombo, C M. et al., The stress-activated protein kinases are major c-Jun amino-terminal kinases activated by ischemia and reperfusion, *J. Biol. Chem.* 1994, 269 (42): 26546-26551.
22. Onishi, I. et al., Activation of c-Jun N-terminal kinase during ischemia and reperfusion in mouse liver, *FEBS Letters* 1997, 420: 201-204
23. Safirstein, R., Renal stress response and acute renal failure *Adv. Ren. Replace Ther.* 1997, 4 (2 Suppl 1): 38-42.
24. Butterfield, L. et al, C-Jun NH2-terminal kinase regulation of the apoptotic response of small cell lung cancer cells to ultraviolet. *The Journal of Biological Chemistry* 1997, 272 (15): 10110-10116.
25. Hu, M. et al., JNK1, JNK2 and JNK3 are p53 N-terminal serine 34 kinases, *Oncogene* 1997, 15: 2277-2287.
26. Xu, X. et al., Constitutively activated JNK is associated with HTLV-1 mediated tumorigenesis, *Oncogene* 1996, 13: 135-142.
27. Chen Y R and Tan T H, The c-Jun N-terminal kinase pathway and apoptotic signaling, *Int. J. Oncol.* 2000, 16(4):651-62.
28. Harding, T. C. et al, Inhibition of JNK by overexpression of the JNK binding domain of JIP-1 prevents apoptosis in sympathetic neurons, *The Journal Of Biological Chemistry* 2001, 276(7):4531-4534.
29. Gennaro, A. R. et al., Remington's Pharmaceutical Sciences. 18th ed. Easton: The Mack Publishing Company, 1995.
30. Green T W and Wuts P G, 1999, $3^{rd}$ Edition, Wiley Ed.
31. Abdel-Magid A F et al., Reductive amination of aldehydes and ketones with sodium triacetoxyborohydride. Studies on direct and indirect reductive amination procedures, *Journal of Organic Chemistry* 1996, 61, 3849-62.
32. Xu, L. et al., Assess the in-vivo activation of signal transduction pathways with Pathdetect® reporting systems, *Strategies* 2001, 14 (1): 17-19.

33. Xu, S. et al., Cloning of rat MEK kinase 1 cDNA reveals an endogenous membrane-associated 195-kDa protein with a large regulatory domain, *Proc. Natl. Acad. Sci USA* 1996, 93:5291-5295.
34. U.S. Pat. No. 5,744,320; Promega Corporation; Apr. 28, 1998
35. Guha, M. and Mackman, N., LPs induction of gene expression in human monocytes, *Cellular Signaling* 2001, 13: 85-94.
36. Fomsgaard, A. et al., Quantification and biological activities of native tumour necrosis factor from LPS-stimulated human monocytes, *APMIS*1990, 98(6): 529-34.
37. Hunter J. L. et al., Animal models of acute ischaemic stroke: can they predict clinically successful neuroprotective drugs? *TIPS* 1995, 16:123-128.
38. Block, F., Global Ischemia And Behavioural Deficits, *Progress in Neurobiology* 1999, 58: 279-295.
39. Gerhard S C and Boast C A, *Behavioral Neuroscience* 1988, 102: 301-303.

What we claim is:

1. A benzsulfonamide according to formula I

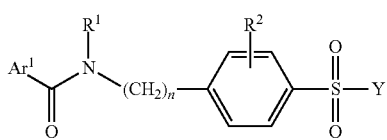

its geometrical isomers, in an optically active form as enantiomers, diastereomers, racemates, or pharmaceutically acceptable salts thereof, wherein $Ar^1$ is selected from the group consisting of an unsubstituted aryl group, an unsubstituted heteroaryl group, a substituted aryl group, and a substituted heteroaryl group;

$R^1$ is hydrogen or a $C_1$-$C_6$-alkyl group;

$R^2$ is hydrogen, —COOR$^3$, —CONR$^3$R$^{3'}$, OH, a $C_1$-$C_4$ alkyl substituted with an OH group, a hydrazido carbonyl group, a sulfate, a sulfonate, an amine or an ammonium salt;

n is either 0 or 1;

Y is a pyrrolidinyl group represented by the following formula:

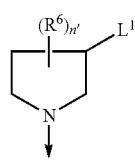

whereby, $L^1$ is selected from the group consisting of $C_1$-$C_6$-alkyl, $C_2$-$C_6$-alkenyl, $C_2$-$C_6$-alkynyl, $C_4$-$C_8$-cycloalkyl optionally containing 1-3 heteroatoms and optionally fused with aryl or heteroaryl, aryl, heteroaryl, aryl-$C_1$-$C_6$-alkyl, heteroaryl-$C_1$-$C_6$-alkyl, —C(O)—OR$^3$, —C(O)—R$^3$, —C(O)—NR$^3$R$^3$, —NR$^3$R$^3$, —NR$^3$C(O)R$^3$, —NR$^3$C(O)NR$^3$R$^3$, —(SO)R$^3$, —(SO$_2$)R$^3$, —NHSO$_2$R$^3$, and —SO$_2$NR$^3$R$^3$, with $R^3$, $R^{3'}$ being substituents independently selected from the group consisting of H, $C_1$-$C_6$-alkyl, $C_2$-$C_6$-alkenyl, aryl, heteroaryl, aryl-$C_1$-$C_6$-alkyl, and heteroaryl-$C_1$-$C_6$-alkyl; and $R^6$ is selected from the group consisting of hydrogen, $C_1$-$C_6$-alkyl, $C_1$-$C_6$-alkoxy, OH, halogen, nitro, cyano, sulfonyl, and oxo (═O), and n' is an integer from 0 to 4.

2. A benzsulfonamide according to claim 1, wherein $Ar^1$ is selected from the group consisting of phenyl, thienyl, furyl, and pyridyl.

3. A benzsulfonamide according to claim 1, wherein $Ar^1$ is a phenyl.

4. A benzsulfonamide according to claim 1, wherein $Ar^1$ is selected from the group consisting of halogenophenyl, nitrophenyl, hydroxyphenyl, alkoxy phenyl, pyridyl, 3,4,-dihydroxyphenyl, thioxo-dihydropyridine or its tautomer, and pyrazole, $R^1$ is hydrogen, n is 1.

5. A benzsulfonamide selected from the group consisting of 4-chloro-N-(3-{[3-(hexylamino)-1-pyrrolidinyl]sulfonyl}phenyl)benzamide;

4-chloro-N-(3-{[3-({2-[3-(trifluoromethyl)phenyl]ethyl}amino)-1-pyrrolidinyl]sulfonyl}phenyl)benzamide;

4-chloro-N-{4-[(3-{[4-(trifluoromethyl)benzyl]amino}-1-pyrrolidinyl)sulfonyl]phenyl}benzamide;

4-chloro-N-(4-{[3-(hexylamino)-1-pyrrolidinyl]sulfonyl}phenyl)benzamide;

4-chloro-N-(4-{[3-({2-[3-(trifluoromethyl)phenyl]ethyl}amino)-1-pyrrolidinyl]sulfonyl}phenyl)benzamide; and 4-chloro-N-{3-[(3-{[4-(trifluoromethyl)benzyl]amino}-1-pyrrolidinyl)sulfonyl]benzyl}benzamide.

6. A method of treating a neuronal disorder, an auto-immune disease, a cancer, a cardiovascular disease, an ischemic condition or renal failure comprising administering an effective amount of a benzsulfonamide according to claim 1 to a subject in need thereof, wherein said neuronal disorder is selected from the group consisting of epilepsy, Alzheimer's disease, Huntington's disease, Parkinson's disease, retinal diseases, spinal cord injury, Multiple Sclerosis, head trauma, and ischemia, wherein said auto-immune disease is selected from the group consisting of inflammatory bowel disease (IBD), rheumatoid arthritis, asthma, septic shock, and transplant rejection, wherein said cancer is selected from the group consisting of breast-cancer, colorectal-cancer, pancreatic cancer, ovarian cancer, prostate cancer, testicular cancer, hepatic cancer, kidney cancer, and lung cancer, wherein said cardiovascular disease is selected from the group consisting of stroke, arterosclerosis, myocardial infarction, and myocardial reperfusion injury, and wherein said ischemic condition is selected from the group consisting of heart reperfusion injury, renal reperfusion injury, kidney reperfusion injury, and brain reperfusion injury.

7. A pharmaceutical composition containing a benzsulfonamide according to claim 1 and a pharmaceutically acceptable carrier, diluent or excipient thereof.

8. A process for the preparation of a benzsulfonamide according to claim 1, wherein a sulfonamide (XIX)

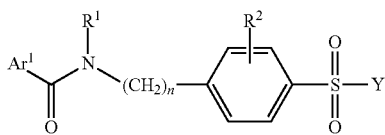

(XIX)

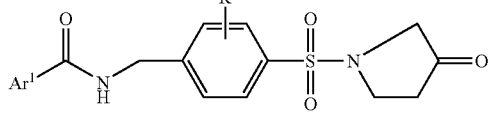

(XIXc)

wherein Ar¹, R¹, R² and n are as defined in claim 1 and Y is a pyrrolidine-3-one, is subjected to a reductive amination using an amine H₂N—R³ with R³ as defined in claim 1.

9. A process according to claim 8, wherein the following steps are performed:

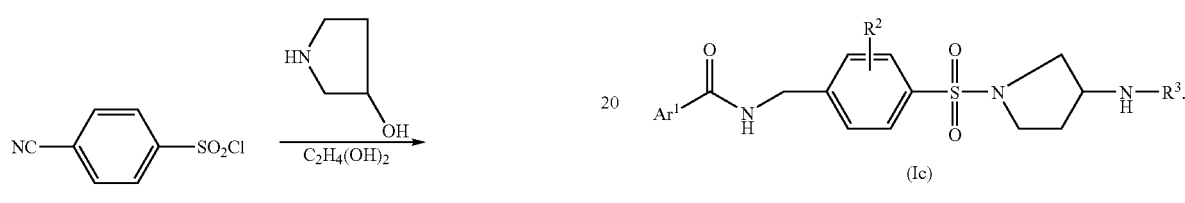

10. A sulfonamide compound of formula (XIX)

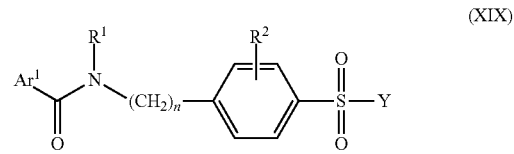

(XIX)

wherein

Ar¹ is an aryl or heteroaryl group;

R¹ is hydrogen or a $C_1$-$C_6$-alkyl group;

R² is hydrogen, —COOR³, —CONR³R³', OH, a $C_1$-$C_4$ alkyl substituted with an OH group, a hydrazido carbonyl group, a sulfate, a sulfonate, an amine or an ammonium salt;

R³ and R³' are independently selected from the group consisting of H, $C_1$-$C_6$-alkyl, $C_2$-$C_6$-alkenyl, aryl, heteroaryl, aryl-$C_1$-$C_6$-alkyl, and heteroaryl-$C_1$-$C_6$-alkyl;

n is either 0 or 1, and

Y is a pyrrolidine-3-one, or a salt thereof.

* * * * *